(12) United States Patent
Luk et al.

(10) Patent No.: US 9,327,060 B2
(45) Date of Patent: May 3, 2016

(54) RAPAMYCIN RESERVOIR ELUTING STENT

(75) Inventors: Andrew Luk, Castro Valley, CA (US); Thai Minh Nguyen, Santa Clara, CA (US); Theodore L. Parker, Danville, CA (US); Gary W. Steese-Bradley, San Jose, CA (US)

(73) Assignee: CARDINAL HEALTH SWITZERLAND 515 GmbH (CH)

( * ) Notice: Subject to any disclaimer, the term of this patent is extended or adjusted under 35 U.S.C. 154(b) by 639 days.

(21) Appl. No.: 12/500,043

(22) Filed: Jul. 9, 2009

(65) Prior Publication Data

US 2011/0009953 A1  Jan. 13, 2011

(51) Int. Cl.
*A61F 2/82* (2013.01)
*A61L 31/10* (2006.01)
*A61F 2/88* (2006.01)
*A61L 31/02* (2006.01)
*A61L 31/16* (2006.01)

(52) U.S. Cl.
CPC . *A61L 31/10* (2013.01); *A61F 2/88* (2013.01); *A61L 31/022* (2013.01); *A61L 31/16* (2013.01); *A61L 2300/416* (2013.01)

(58) Field of Classification Search
CPC .............. A61L 31/16; A61L 2300/416; A61L 2300/432; A61L 27/54; A61F 2/88; A61F 2002/91525; A61F 2/885; A61F 2002/91508; A61F 2250/0068
USPC ............ 623/1.15, 1.22, 1.39, 1.42, 1.43, 1.45
See application file for complete search history.

(56) References Cited

U.S. PATENT DOCUMENTS

| 3,929,992 | A | 12/1975 | Sehgal et al. |
| 6,241,762 | B1 | 6/2001 | Shanley |
| 6,293,967 | B1 | 9/2001 | Shanley |
| 6,572,644 | B1* | 6/2003 | Moein ........................ 623/1.15 |
| 6,764,507 | B2 | 7/2004 | Shanley et al. |
| 2005/0203610 | A1* | 9/2005 | Tzeng ........................ 623/1.22 |
| 2006/0020325 | A1 | 1/2006 | Burgermeister et al. |
| 2006/0155360 | A1 | 7/2006 | Calisse et al. |
| 2007/0150048 | A1* | 6/2007 | Tischler ...................... 623/1.22 |
| 2008/0097579 | A1* | 4/2008 | Shanley et al. ............. 623/1.42 |

(Continued)

FOREIGN PATENT DOCUMENTS

| EP | 1952789 A1 | 6/2008 |
| EP | 1952789 | 8/2008 |

(Continued)

OTHER PUBLICATIONS

Berk, B.C. et al., "Pharmacologic Roles of Heparin and Glucocorticoids to Prevent Restenosis After Coronary Angioplasty", J. Am. Coll. Cardio. vol. 17, No. 6, pp. 111B-117B, 1991.

(Continued)

*Primary Examiner* — Brian Pellegrino
(74) *Attorney, Agent, or Firm* — Dergosits & Noah LLP; Todd A. Noah

(57) ABSTRACT

Implantable medical devices may be utilized to locally deliver one or more drugs or therapeutic agents to treat a wide variety of conditions, including the treatment of the biological organism's reaction to the introduction of the implantable medical device. These therapeutic agents may be released under controlled and directional conditions from a stent so that the one or more therapeutic agents reach the correct target area, for example, the surrounding tissue.

6 Claims, 19 Drawing Sheets

(56) References Cited

U.S. PATENT DOCUMENTS

| | | | |
|---|---|---|---|
| 2009/0125096 A1 | 5/2009 | Chu et al. | |
| 2009/0163995 A1 | 6/2009 | Shanley et al. | |
| 2010/0280600 A1* | 11/2010 | Dave et al. | 623/1.42 |

FOREIGN PATENT DOCUMENTS

| | | |
|---|---|---|
| EP | 2213264 | 8/2010 |
| EP | 2246076 | 11/2010 |
| EP | 2272550 | 12/2013 |
| GB | 1454109 | 10/1976 |
| WO | 02/32347 | 4/2002 |
| WO | WO 2004/110302 A2 | 12/2004 |
| WO | 2006007473 | 1/2006 |

OTHER PUBLICATIONS

Campbell and Campbell "Phenotypic Modulation of Smooth Muscle Cells in Primary Culture", (Table of Contents), Chapter 2, vol. 1, pp. 39-52 (1985).
Campbell and Campbell "Cell Biology of Smooth Muscle in Culture: Implications for Atherogenesis", Inter. Angio, 6, p. 73 (1987).
Chang, M.W. et al., "Adenovirus-Mediated Over-Expression of the Cyclin/Cyclin-Dependent Kinase Inhibitor, p21 Inhibits Vascular Smooth Muscle Cell Proliferation and Neointimal Formation in the Rat Carotid Artery Model of Balloon Angioplasty", J. Clin. Invest. vol. 96, pp. 2260-2268 (1995).
Clowes, A.W. et al., "Suppression by Heparin of Smooth Muscle Cell Proliferation in Injured Arteries", Nature, vol. 265, pp. 625-626 (1977).
Clowes, A.W. et al, "Kinetics of Cellular Proliferation after Arterial Injury", Laboratory Investigation, vol. 52, No. 6, pp. 611-616 (1985).
Clowes, A.W. et al., "Kinetics of Cellular Proliferation after Arterial injury IV. Heparin Inhibits Rat Smooth Muscle Mitogenesis and Migration", Circulation Research, vol. 58, No. 6, pp. 839-845 (1986).
Clowes and Schwartz, "Significance of Quiescent Smooth Muscle Migration in the Injured Rat Carotid Artery", Cir. Res. 56: 139-145 (1985).
Colburn, M.D. et al., "Dose Responsive Suppression of Myointimal Hyperplasia by Dexamethasone", J. Vasc. Surg. vol. 15, No. 3, pp. 510-518 (1992).
Currier, J.W. et al., "Colchicine Inhibits Restenosis After Iliac Angioplasty in the Atherosclerotic Rabbit", Supplement II Circulation vol. 80, No. 4, II-66 (1989).
Edelman, E., et al. "Pathobiologic Responses to Stenting", American Journal of Cardiology vol. 91, Issue 7, Suppl. 1 (Apr. 1998) pp. 4E-6E.
Farb, A. et al., "Vascular Smooth Muscle Cell Cytotoxicity and Sustained Inhibition of Neointimal Formation by Fibroblast Growth Factor 2-Saporin Fusion Protein", Circ. Res. vol. 80, No. 4, pp. 542-550 (1997).
Ferns, G.A. et al., "Inhibition of Neointimal Smooth Muscle Accumulation After Angioplasty by an Antibody to PDGF", Science, vol. 253, pp. 1129-1132 (1991).
Fischman, D., et al. "A Randomized Comparison of Coronary-Stent Placement and Balloon Angioplasty in the Treatment of Coronary Artery Disease", The New England Journal of Medicine, vol. 331:496-501 (1994).
Franklin and Faxon, "Pharmacologic Prevention of Restenosis After Coronary Angioplasty: Review of the Randomized Clinical Trials", Coronary Artery Disease, vol. 4, No. 3 (Mar. 1993).
Fukuyama J., et al., "Tranilast Suppresses the Vascular Intimal Hyperplasia After Balloon Injury in Rabbits Fed on a High-Cholesterol Diet", European Journal of Pharmacology 318, pp. 327-332 (1996).
Guyton, J.R. et al., "Inhibition of Rat Arterial Smooth Muscle Cell Proliferation by Heparin", Circulation Research, vol. 46, No. 5, pp. 625-634 (1980).
Hanson, S.R. et al., "Interruption of Acute Platelet-Dependent Thrombosis by the Synthetic Antithrombin D-phenylalanyl-L-prolyl-L-arginyl Chloromethyl Ketone"; Proc. Natl. Acad. Sci. USA (May 1988) 85: 3184-3188.

Hansson, G.K., et al., "Interferon-γ Inhibits Arterial Stenosis After Injury" Circulation, vol. 84, No. 3, pp. 1266-1272 (1991).
Jonasson, L. et al., "Cyclosporin A Inhibits Smooth Muscle Proliferation in the Vascular Response to Injury", Proc. Natl. Acad. Sci. USA vol. 85, pp. 2303-2306, (1988).
Kunishima, T., et al. "A Randomized Trial of Aspirin Versus Cilostazol Therapy After Successful Coronary Stent Implantation", Clinical Therapeutics, vol. 19, No. 5 (1997) pp. 1058-1066.
Lang R., et al. "Effects of Okadaic Acid and ATPγS on Cell Length and $CA^{2+}$—Channel Currents Recorded in Single Smooth Muscle Cells of the Guinea-Pig Taenia Caeci", Br. J. Pharmacol. 104, p. 331-336 (1991).
Liu, M.W. et al., "Trapidil in Preventing Restenosis After Balloon Angioplasty in the Atherosclerotic Rabbit", Circ. vol. 81, No. 3, pp. 1089-1093 (1990).
Lundergan, C.F. et al., "Peptide Inhibition of Myointimal Proliferation by Angiopeptin, a Somatostatin Analogue", JACC vol. 17(Supp. B), No. 6. pp. 132B-136B (1991).
Majesky, M.W. et al., "Heparin Regulates Smooth Muscle S Phase Entry in the Injured Rat Carotid Artery", Circ. Res. vol. 61, No. 2, pp. 296-300 (1987).
Mak and Topol, "Clinical Trials to Prevent Restenosis after Percutaneous Coronary Revascularization", Department of Cardiolog, Cleveland Clinical Foundation, Ohio p. 255 (1991).
Marx, S.O., et al., "Rapamycin-FKBP Inhibits Cell Cycle Regulators of Proliferation in Vascular Smooth Muscle Cells", Circ. Res., vol. 76, No. 3, pp. 412-417 (1995).
Mintz, G., et al. "Limitations of Angiography in the Assessment of Plaque Distribution in Coronary Artery Disease", Circulation (1996) vol. 93 pp. 924-931.
Nemecek, G.M. et al., "Terbinafine Inhibits the Mitogenic Response to Platelet-Derived Growth Factor in Vitro and Neointimal Proliferation in Vivo", J. Pharmacol. Exp. Thera. vol. 248, No. 3, pp. 1167-1174 (1989).
Okada, T. et al., Localized Release of Perivascular Heparin Inhibits Intimal Proliferation after Endothelial Injury without Systemic Anticoagulation, Neurosurgery, vol. 25, No. 6, pp. 892-898 (1989).
Pompa, J., et al. "Clinical Trials of Restenosis After coronary Angioplasty", American Heart Association, Circulation, (1991) 84:1426-1436.
Powell, J.S. et al., Inhibitors of Antiotensin-Converting Enzyme Prevent Myointimal Proliferation After Vascular Injury, Science, vol. 245, pp. 186-188 (1989).
Serruys P., et al. "Evaluation of Ketanserin in the Prevention of Restenosis After Percutaneous Transuminal Coronary Angioplasty. A Multicenter Randomized Double-Blind Placebo-Controlled Trial", American Heart Association, Circulation, 88, p. 1588 (1993).
Serruys, P., et al. "A Comparison of Balloon-Expandable-Stent Implantation with Balloon Angioplasty in Patients with Coronary Artery Disease", New England Journal of Medicine, vol. 331:489-495 (1994).
Serruys, P., et al. "Heparin-Coated Palmaz-Schatz Stents in Human Coronary Arteries: Early Outcome of the Benestent-II Pilot Study", Circulation of the American Heart Association, vol. 93(3) p. 412-422 (1996).
Simons, M. et al., "Antisense c-*myb* oligonucleotides inhibit intimal arterial smooth muscle cell accumulation in vivo", Nature, vol. 359, pp. 67-70 (1992).
Snow, A.D. et al., "Heparin Modulates the Composition of the Extracellular Matrix Domain Surrounding Arterial Smooth Muscle Cells", vol. 137, No. 2, pp. 313-330, (1990).
Sollot, S.J. et al., "Taxol Inhibits Neointimal Smooth Muscle Cell Accumulation after Angioplasty in the Rat", J. Clinical Investigation, Inc. vol. 95, pp. 1869-1876, (1995).
Take, S., et al. "Effect of Cilostazol in Preventing Restenosis After Percutaneous Transluminal Coronary Angioplasty", Am. J. Cardiol. (1997) vol. 79 pp. 1097-1099.
Tanaka, H., et al. "Sustained Activation of Vascular Cells and Leukocytes in the Rabbit Aorta After Balloon Injury", Circulation, vol. 88, 1788-1803 (1993).
Tardif, J-C., et al. "Probucol and Multivitamins in the Prevention of Restenosis After Coronary Angioplasty", New England Journal of Medicine, vol. 337:365-372 (1997).

(56) References Cited

OTHER PUBLICATIONS

Teirstein, P., et al. "Catheter-Based Radiotherapy to Inhibit Restenosis After Coronary Stenting", The New England Journal of Medicine, vol. 336 p. 1697 (Jun. 1997).

Tsuchikane, T. et al. "Impact of Cilostazal on Restenosis After Percutaneous Coronary Balloon Angioplasty", Circulation (1999) vol. 11 pp. 21-26.

Weinberger, J. et al., "Intracoronary Irradiation: Dose Response for the Prevention of Restenosis in Swine", Int. J. Radiation Onc. Biol. Phys. vol. 36, No. 4, pp. 767-775, 1996.

Yokoi, H., et al. "Effectiveness of an Antioxidant in Preventing Restenosis After Percutaneous Transluminal Coronary Angioplasty: The Probucol Angioplasty Restenosis Trial", JACC, vol. 30, No. 4 (1997) pp. 855-862.

Office Action in corresponding Chinese Patent Application No. 201010228936.1 dated Apr. 15, 2013.

Office Action in corresponding Israeli Patent Application No. 206190 dated Dec. 3, 2014.

Office Action dated Oct. 22, 2014 in corresponding Russian Patent Application No. 2010128382/14.

Zalessky, V.N., et al. "Molecular-cellular mechanisms of intra-stent restenosis and contemporary endoprosthesis-associated medical technologies of its local biotheraphy(results and promises)," Ukrainskiy Meditsinskiy Chasopis, No. 4 (60), 2007, pp. 30-41; see pp. 30-34 [online] [Retrieved Jun. 8, 2914 from the internet: http://www.umj.com.ua/wp-content/uploads/archive/60/pdf/88__rus.pdf.

Gershlick, A., et al., "Inhibition of restenosis with a paclitaxel-eluting, polymer-free coronary stent: the European evaluation of paclitaxel Eluting Stent (ELUTES) trial," Circulation, Feb. 3, 2004; 109 (4): 487-93, Epub Jan. 26, 2004, Abstract; retrieved Jul. 8, 2014 from Pub Med PMID: 14744971.

Rinker, A., et al., "Angiographic results of a Tacrolimus-eluting stent in acute coronary syndrome lesions," Clin. Res. Cardiol., Feb. 2009; 98 (2): 89-93, Abstract, retrieved Jul. 8, 2014 from PubMed PMID: 18853086.

Ortolani, P., et al. "Randomized comparative trial of a thin-strut bare cobalt-chromium stent versus a sirolimus-eluting stent for coronary revascularization." Catheter Cardiovasc. Interv. May 1, 2007; 69 (6): 790-8, Abstract retrieved Jun. 8, 2014 from PubMed PMID: 17290437.

Xu, B., et al. "Sirolimus-eluting cobalt-chromium stents: Two year clinical results from first-in-man study on the Firebird 2 stent." Clin. Med. J. (Engl) Mar. 20, 2008; 121 (6): 492-7; Free full text retrieved Jun. 8, 2014 from PubMed PMID: 18364131.

Feng, B., et al. "Pharmacodynamics of China-made rapamycin-polylactide-co-glycolide peripheral arterial eluting stent membrane: in vitro experiments."

Notice of Reexamination for China Patent Application No. 201010228936.1; mailed on Jan. 11, 2016.

\* cited by examiner

In vitro drug release from combined drug coating

In vitro drug release from layered drug coating

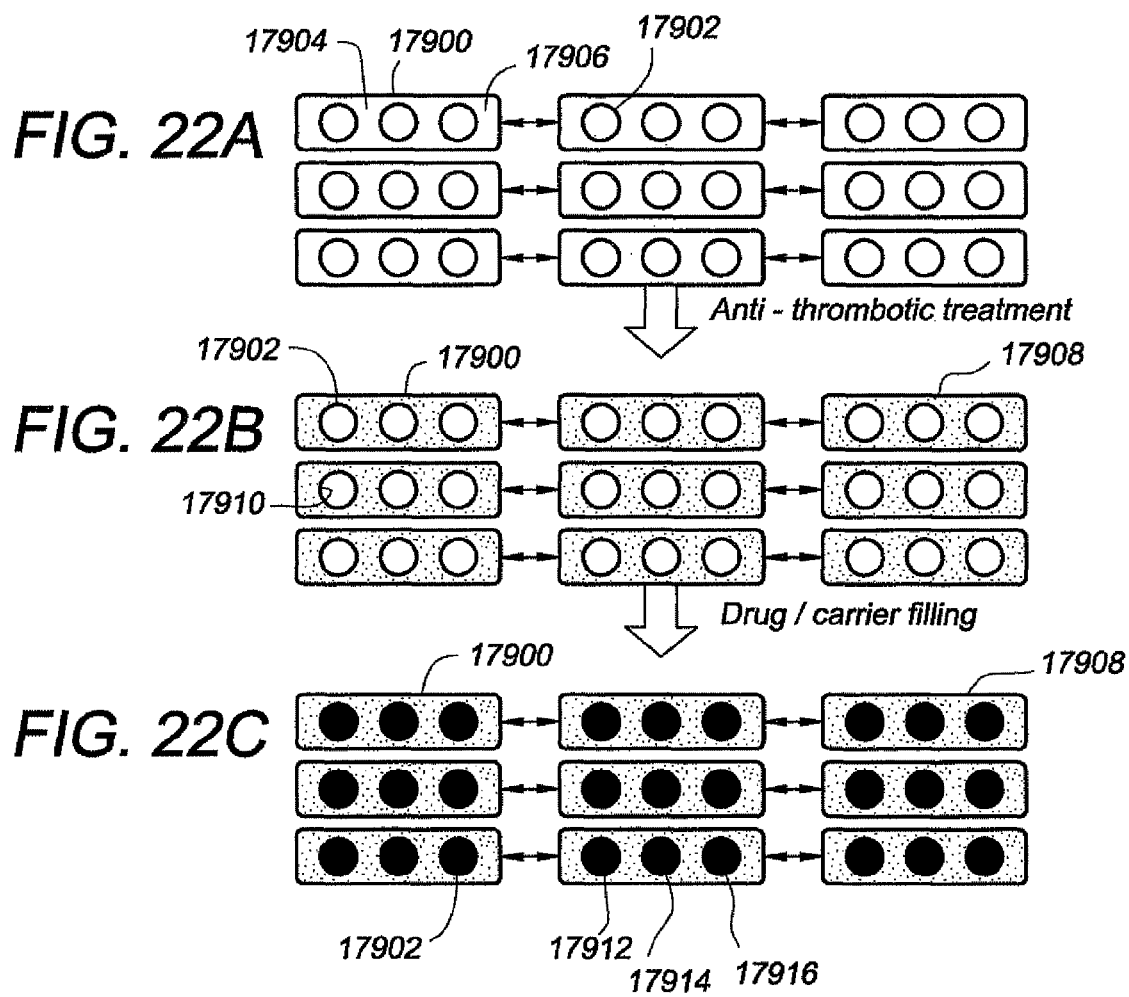

SS or L-lactide

RR or D-lactide

RS or meso-lactide poly (L-lactide)

poly (D-lactide)

RAPAMYCIN RESERVOIR ELUTING STENT

BACKGROUND OF THE INVENTION

1. Field of the Invention

The present invention relates to the local administration of therapeutic agents and/or therapeutic agent combinations for the prevention and treatment of vascular disease, and more particularly to intraluminal medical devices for the local delivery of therapeutic agents and/or therapeutic agent combinations.

2. Discussion of the Related Art

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans, which are believed to be responsible for maintaining smooth muscle cells in the contractile phenotypic state (Campbell and Campbell, 1985).

Upon pressure expansion of an intracoronary balloon catheter during angioplasty, smooth muscle cells and endothelial cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll. Cardiol. 17: 111B-117B, 1991), ionizing radiation (Weinberger, J. et al., Int. J. Rad. Onc. Biol. Phys. 36: 767-775, 1996), fusion toxins (Farb, A. et al., Circ. Res. 80: 542-550, 1997) antisense oligionucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty.

SUMMARY OF THE INVENTION

The rapamycin reservoir eluting stent of the present invention overcomes the limitations of the prior art devices as set forth above.

In accordance with one exemplary embodiment, the present invention is directed to a drug filled reservoir eluting implantable medical device. The drug filled reservoir eluting implantable medical device comprising a stent comprising a helical mid section formed from a substantially sinusoidal arrangement of alternating struts configured to have a constant helical pitch connected via ductile hinges, first and second ring end sections having a substantially sinusoidal arrangement of alternating struts connected via ductile hinges, and first and second transition sections formed from a substantially sinusoidal arrangement of alternating struts configured to have a variable helical pitch connected via ductile hinges, the first and second ring end sections being connected to the helical mid section via the first and second transition sections respectively, wherein at least one of the struts comprise at least one reservoir and a composition comprising an mTOR inhibitor and a biodegradable polymer, the composition being deposited in the at least one reservoir and configured to elute the mTOR inhibitor in the abluminal direction.

The stent of the present invention comprises a unique design as briefly described above and may be formed from a cobalt-chromium alloy. The stent is designed to maintain vessel patency and to locally deliver sirolimus to the surrounding arterial tissue for the prevention and treatment of vascular disease, including restenosis. The sirolimus is incorporated into a polymeric matrix, preferably along with a stabilizing agent such as butylated hydroxyl toluene. Each reservoir in the stent is filled with a solution comprising the sirolimus, the polymer, the stabilizing agent and the solvent. The filling process includes a series of deposition steps followed by drying steps to remove the solvent. The construct of each reservoir functions to minimize the elution of sirolimus into the bloodstream while maximizing it into the arterial tissue surrounding the stent.

The stent of the present invention provides for the controlled, sustained and local delivery of sirolimus directly into the surrounding tissue with minimal loss into the blood. The stent is preferably fabricated from a cobalt-chromium alloy that is less brittle and has enhanced ductility and toughness as well as increased durability as compared to stents fabricated from other materials.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 22A, 22B, 22C are partial diagrammatic representations of an alternate exemplary embodiment of an expandable medical device.

DETAILED DESCRIPTION OF THE PREFERRED EMBODIMENTS

Figure 1:
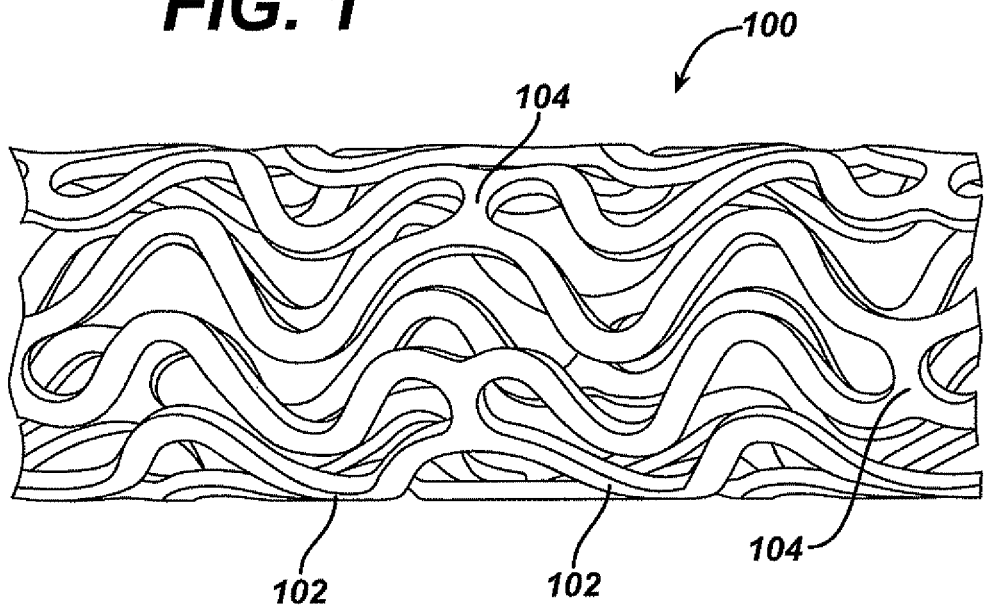
FIG. 1 is a view along the length of a stent (ends not shown) prior to expansion showing the exterior surface of the stent and the characteristic banding pattern.

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits. In addition, various methods and devices will be described for the effective delivery of the coated medical devices.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/III$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As stated herein, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the invention, for simplicity, a limited number of stents will be described in exemplary embodiments of the present invention. The skilled artisan will recognize that any number of stents may be utilized in connection with the invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

FIG. 1 illustrates an exemplary stent 100 which may be utilized in accordance with an exemplary embodiment of the invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration that is circumferentially or radially rigid. The stent 100 is axially flexible and when flexed at a band, the stent 100 avoids any externally protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one exemplary embodiment, expansion may be affected in a blood vessel by a balloon catheter, where the final diameter of the stent 100 is a function of the diameter of the balloon catheter used.

It should be appreciated that a stent 100 in accordance with the invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
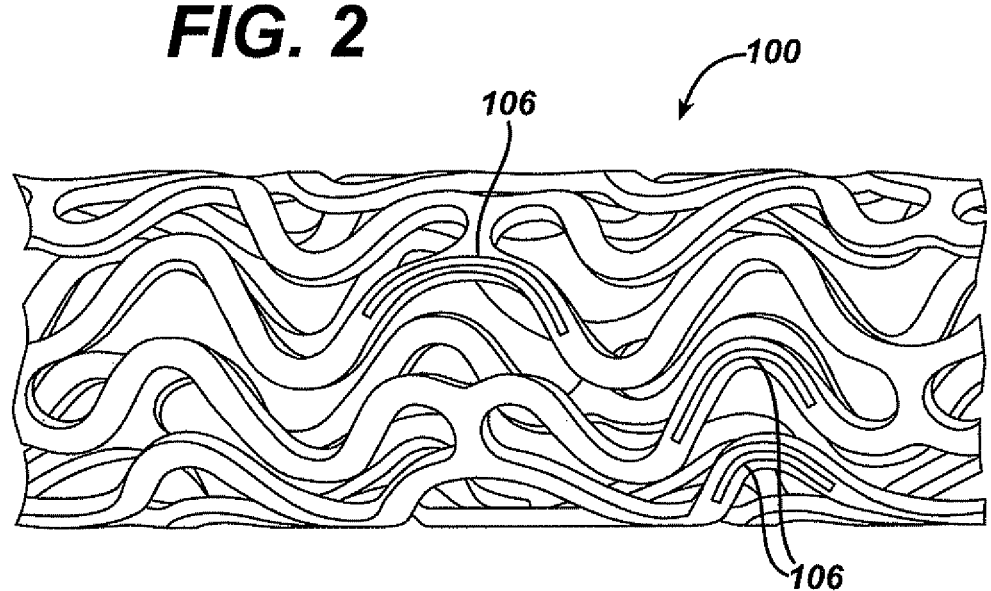
FIG. 2 is a perspective view along the length of the stent of FIG. 1 which is modified to include reservoirs.

FIG. 2 illustrates an exemplary embodiment of the invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Rapamycin is a macrocyclic triene antibiotic produced by *Streptomyces hygroscopicus* as disclosed in U.S. Pat. No. 3,929,992. It has been found that a rapamycin among other things inhibits the proliferation of vascular smooth muscle cells in vivo. Accordingly, rapamycin or rapamycins may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycins function to inhibit smooth muscle cell proliferation and do not interfere with the re-endothelialization of the vessel walls.

Rapamycins reduce vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, a rapamycin includes rapamycin and all analogs, derivatives and conjugates that bind to FKBP12, and other immunophilins and possesses the same pharmacologic properties as rapamycin including inhibition of TOR or mTOR.

Although the anti-proliferative effects of a rapamycin may be achieved through systemic use, superior results may be achieved through the local delivery of the compound. Essentially, a rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycins may be incorporated onto or affixed to the stent in a number of ways. In one exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Rapamycin coatings may be applied to stents by a dip, spray or spin coating method, and/or any combination of these methods. Various polymers may be utilized. For example, poly(ethylene-co-vinyl acetate) and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. A barrier or top coat may also be applied to modulate the dissolution of the rapamycin from the polymer matrix.

It is important to note that the stent, as described above, may be formed from any number of materials, including various metals, polymeric materials and ceramic materials. Accordingly, various technologies may be utilized to immobilize the various drugs, agent, and compound combinations thereon. Specifically, in addition to the polymeric matricies described above biopolymers may be utilized. Biopolymers may be generally classified as natural polymers, while the above-described polymers may be described as synthetic polymers. Exemplary biopolymers, which may be utilized include, agarose, alginate, gelatin, collagen and elastin. In addition, the drugs, agents or compounds may be utilized in conjunction with other percutaneously delivered medical devices such as grafts and profusion balloons.

The molecular events that are responsible for the actions of a rapamycin, a known anti-proliferative, which acts to reduce the magnitude and duration of neointimal hyperplasia, are still being elucidated. It is known, however, that a rapamycin enters cells and binds to a high-affinity cytosolic protein called FKBP12. The complex of the rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that a rapamycin reduces restenosis by inhibiting neointimal hyperplasia. However, there is evidence that the rapamycin may also inhibit the other major component of restenosis, namely, negative remodeling. Remodeling is a process whose mechanism is not clearly understood but which results in shrinkage of the external elastic lamina and reduction in luminal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural time point to four-month and twelve-month follow-ups are reflective of remodeling changes.

Evidence that rapamycins exert an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that the rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis (%, mean ± SD and "n=") In Patients Who Received a Rapamycin-Coated Stent

| Coating Group | Post Placement | 4-6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n=) | 4-Month Follow-Up (n=) | 12-Month Follow-Up (n=) |
|---|---|---|---|
| Mean proximal vessel area (mm²) | 16.53 ± 3.53 (27) | 16.31 ± 4.36 (28) | 13.96 ± 2.26 (13) |
| Mean distal vessel area (mm²) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycins may also affect the translation of key proteins involved in collagen formation or metabolism.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator. In other embodiments, an injection needle may be utilized.

Rapamycins may also be delivered systemically using an oral dosage form or a chronic injectible depot form or a patch to deliver the rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of the rapamycin into the vascular wall from a nonerodible polymeric stent coating in a range of doses (35-430 ug/15-18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm$^2$) | % Change From Polyme | % Change From Metal |
|---|---|---|---|---|---|---|---|
| | Porcine | | | | | | |
| 98009 | 14 days | Metal | | 8 | 2.04 ± 0.17 | | |
| | | 1X + rapamycin | 153 μg | 8 | 1.66 ± 0.17* | −42% | −19% |
| | | 1X + TC300 + rapamycin | 155 μg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 μg | 8 | 2.81 ± 0.34 | | +23% |
| | | 1X + TC100 + rapamycin | 120 μg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 μg | 11 | 2.84 ± 0.31*** | −43% | −38% |
| | | 3X + rapamycin | 430 μg | 12 | 3.06 ± 0.17*** | −39% | −33% |
| | | 3X + rapamycin | 157 μg | 12 | 2.77 ± 0.41*** | −45% | −39% |
| 99011 | 28 days | Metal | | 11 | 3.09 ± 0.27 | | |
| | | | | 11 | 4.52 ± 0.37 | | |
| | | 1X + rapamycin | 189 μg | 14 | 3.05 ± 0.35 | | −1% |
| | | 3X + rapamycin/dex | 182/363 μg | 14 | 2.72 ± 0.71 | | −12% |
| 99021 | 60 days | Metal | | 12 | 2.14 ± 0.25 | | |
| | | 1X + rapamycin | 181 μg | 12 | 2.95 ± 0.38 | | +38% |
| 99034 | 28 days | Metal | | 8 | 5.24 ± 0.58 | | |
| | | 1X + rapamycin | 186 μg | 8 | 2.47 ± 0.33** | | −53% |
| | | 3X + rapamycin/dex | 185/369 μg | 6 | 2.42 ± 0.64** | | −54% |
| 20001 | 28 days | Metal | | 6 | 1.81 ± 0.09 | | |
| | | 1X + rapamycin | 172 μg | 5 | 1.66 ± 0.44 | | −8% |
| 20007 | | | | | | | |
| | 30 days | Metal | | 9 | 2.94 ± 0.43 | | |
| | | 1XTC + rapamycin | 155 μg | 10 | 1.40 ± 0.11* | | −52%* |
| | Rabbit | | | | | | |
| 99019 | 28 days | Metal | | 8 | 1.20 ± 0.07 | | |
| | | EVA/BMA 1X | | 10 | 1.26 ± 0.16 | | +5% |
| | | 1X + rapamycin | 64 μg | 9 | 0.92 ± 0.14 | −27% | −23% |
| | | 1X + rapamycin | 196 μg | 10 | 0.66 ± 0.12*** | −48% | −45% |
| 99020 | 28 days | Metal | | 12 | 1.18 ± 0.10 | | |
| | | EVA/BMA 1X + rapamycin | 197 μg | 8 | 0.81 ± 0.16 | | −32% |

[1]Stent nomenclature: EVA/BMA 1X, 2X, and 3X signifies approx. 500 μg, 1000 μg, and 1500 μg total mass (polymer + drug), respectively. TC, top coat of 30 μg, 100 μg, or 300 μg drug-free BMA; Biphasic; 2 × 1X layers of rapamycin in EVA/BMA separated by a 100 μg drug-free BMA layer.
[2]0.25 mg/kg/d × 14 d preceded by a loading dose of 0.5 mg/kg/d × 3 d prior to stent implantation.
*$p < 0.05$ from EVA/BMA control.
**$p < 0.05$ from Metal;
Inflammation score: (0 = essentially no intimal involvement; 1 = <25% intima involved; 2 = ≥25% intima involved; 3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm$^2$) | % Change From Polyme | % Change From Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 μg | 10 | 0.29 ± 0.03 | | −24% | 1.08 ± 0.04 |
| | 30 days | Metal | | 9 | 2.94 ± 0.43 | | | 0.11 ± 0.08 |
| | | 1XTC + rapamycin | 155 μg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 μg | 10 | 3.03 ± 0.29 | | −12% | 0.80 ± 0.23 |
| | | 1X + rapamycin | 171 μg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 μg | 10 | 3.34 ± 0.31 | | −8% | 1.50 ± 0.34 |
| | | 1X + rapamycin | 171 μg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising a rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

TABLE 5.0

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent Diameter Stenosis (%) | | |
| Mean ± SD (N) | 8.9% ± 6.1% (15) | [5.8%, 12.0%] |
| Range (min, max) | (−3.0%, 22.0%) | |
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycins produce an unexpected benefit in humans when delivered from a stent by causing a profound reduction in in-stent neointimal hyperplasia that is sustained for at least one year. The magnitude and duration of this benefit in humans is not predicted from animal model data. Rapamycins used in this context includes rapamycin and all analogs, derivatives and conjugates that bind FKBP12 and possess the same pharmacologic properties as a rapamycin.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and the polymer coating that controls the release of the drug is important in the effectiveness of the drug.

As stated above, rapamycins reduce vascular hyperplasia by antagonizing smooth muscle proliferation in response to mitogenic signals that are released during angioplasty injury. Also, it is known that rapamycins prevent T-cell proliferation and differentiation when administered systemically. It has also been determined that rapamycins exert a local inflammatory effect in the vessel wall when administered from a stent in low doses for a sustained period of time (approximately two to six weeks). The local anti-inflammatory benefit is profound and unexpected. In combination with the smooth muscle anti-proliferative effect, this dual mode of action of rapamycins may be responsible for its exceptional efficacy.

Accordingly, rapamycins delivered from a local device platform, reduces neointimal hyperplasia by a combination of anti-inflammatory and smooth muscle anti-proliferative effects. Local device platforms include stent coatings, stent sheaths, grafts and local drug infusion catheters or porous balloons or any other suitable means for the in situ or local delivery of drugs, agents or compounds.

The anti-inflammatory effect of a rapamycin is evident in data from an experiment, illustrated in Table 6, in which a rapamycin delivered from a stent was compared with dexamethasone delivered from a stent. Dexamethasone, a potent steroidal anti-inflammatory agent, was used as a reference standard. Although dexamethasone is able to reduce inflammation scores, a rapamycin is far more effective than dexamethasone in reducing inflammation scores. In addition, a rapamycin significantly reduces neointimal hyperplasia, unlike dexamethasone.

TABLE 6.0

| Group Rapamycin Rap | N= | Neointimal Area (mm$^2$) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin (Rap) | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*= significance level P < 0.05

Rapamycins have also been found to reduce cytokine levels in vascular tissue when delivered from a stent. The data in FIG. 1 illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycins may be shown to inhibit local inflammatory events in the vessel it is believed that this could explain the unexpected superiority of rapamycins in inhibiting neointima.

As set forth above, a rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycins suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving a rapamycin delivered locally from a stent. The invention expands upon the mechanism of rapamycins to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as $P_{27}^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed above may be administered either systemically, for example, orally, intravenously, intramuscularly, subcutaneously, nasally or intradermally, or locally, for example, stent coating, stent covering or local delivery catheter. In addition, the drugs or agents discussed above may be formulated for fast-release or slow release with the objective of maintaining the drugs or agents in contact with target tissues for a period ranging from three days to eight weeks.

As set forth above, the complex of a rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of a rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either systemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

Further, insulin supplemented diabetic patients receiving rapamycin eluting vascular devices, such as stents, may exhibit a higher incidence of restenosis than their normal or non-insulin supplemented diabetic counterparts. Accordingly, combinations of drugs may be beneficial.

The local delivery of drugs, agents or compounds from a stent has the following advantages; namely, the prevention of vessel recoil and remodeling through the scaffolding action of the stent and the drugs, agents or compounds and the prevention of multiple components of neointimal hyperplasia. This local administration of drugs, agents or compounds to stented coronary arteries may also have additional therapeutic benefit. For example, higher tissue concentrations would be achievable than that which would occur with systemic administration, reduced systemic toxicity, and single treatment and ease of administration. An additional benefit of drug therapy may be to reduce the dose of the therapeutic compounds, thereby limiting their toxicity, while still achieving a reduction in restenosis.

In yet another alternate exemplary embodiment, a rapamycin may be utilized in combination with cilostazol. Cilostazol {6[4-(1-cyclohexyl-1H-tetrazol-5-yl)-butoxy]-3,4-dihydro-2-(1H)-quinolinone} is an inhibitor of type III (cyclic GMP-inhibited) phosphodiesterase and has anti-platelet and vasodilator properties. Cilostazol was originally developed as a selective inhibitor of cyclic nucleotide phosphodiesterase 3. Phosphodiesterase 3 inhibition in platelets and vascular smooth muscle cells was expected to provide an anti-platelet effect and vasodilation; however, recent preclinical studies have demonstrated that cilostazol also possesses the ability to inhibit adenosine uptake by various cells, a property that distinguishes cilostazol from other phosphodiesterase 3 inhibitors, such as milrinone. Accordingly, cilostazol has been shown to have unique antithrombotic and vasodilatory properties based upon a number of novel mechanisms of action. Other drugs in the inhibitors of type III phosphodiesterase class include milrinone, vesnarionone, enoximone, pimobendan and meribendan.

Studies have also shown the efficacy of cilostazol in reducing restenosis after the implantation of a stent. See, for example, Matsutani M., Ueda H. et al.: "Effect of cilostazol in preventing restenosis after percutaneous transluminal coronary angioplasty, Am. J. Cardiol 1997, 79:1097-1099, Kunishima T., Musha H., Eto F., et al.: A randomized trial of aspirin versus cilostazol therapy after successful coronary stent implantation, Clin Thor 1997, 19:1058-1066, and Tsuchikane E. Fukuhara A., Kobayashi T., et al.: Impact of cilostazol on restenosis after percutaneous coronary balloon angioplasty, Circulation 1999, 100:21-26.

In accordance with the invention, cilostazol may be configured for sustained release from a medical device or medical device coating to help reduce platelet deposition and thrombosis formation on the surface of the medical device. As described herein, such medical devices include any short and long term implant in constant contact with blood such as cardiovascular, peripheral and intracranial stents. Optionally, cilostazol may be incorporated in an appropriate polymeric coating or matrix in combination with a rapamycin or other potent anti-restenotic agents.

The incorporation and subsequent sustained release of cilostazol from a medical device or a medical device coating will preferably reduce platelet deposition and thrombosis formation on the surface of the medical device. There is, as described above, pre-clinical and clinical evidence that indicates that cilostazol also has anti-restenotic effects partly due to its vasodilating action. Accordingly, cilostazol is efficacious on at least two aspects of blood contacting devices such as drug eluting stents. Therefore, a combination of cilostazol with another potent anti-restenotic agent including a rapamycin, such as sirolimus, its analogs, derivatives, congeners and conjugates or paclitoxel, its analogs, derivatives, congeners and conjugates may be utilized for the local treatment of cardiovascular diseases and reducing platelet deposition and thrombosis formation on the surface of the medical device. Although described with respect to stents, it is important to note that the drug combinations described with respect to this exemplary embodiment may be utilized in connection with any number of medical devices, some of which are described herein.

Figure 3:
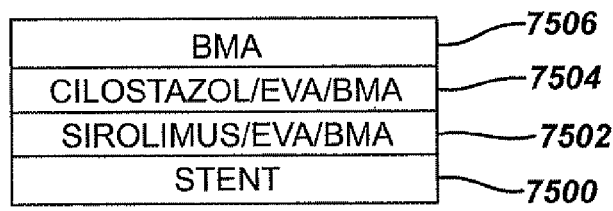
FIG. 3 is a diagrammatic representation of a first exemplary embodiment of a stent coated with a combination of sirolimus and cilostazol.

FIG. 3 illustrates a first exemplary configuration of a combination of cilostazol and a rapamycin on a stent. In this exemplary embodiment, the stent is a Bx Velocity® stent available from Cordis Corporation. In this particular configuration, the stent 7500 is coated with three layers. The first layer or inner layer 7502 comprises one hundred eighty (180 µg) micrograms of sirolimus which is equivalent to forty-five (45) percent by weight of the total weight of the inner layer 7502 and a copolymer matrix of, polyethelene-co-vinylacetate and polybutylmethacrylate, EVA/BMA which is equivalent to fifty-five (55) percent by weight of the total weight of the inner layer 7502. The second layer or outer layer 7504 comprises one hundred (100 µg) micrograms of cilostazol which is equivalent to forty-five (45) percent by weight of the total weight of the outer layer 7504 and a copolymer matrix of EVA/BMA which is equivalent to fifty-five (55) percent by weight of the total weight of the outer layer 7504. The third layer or diffusion overcoat 7506 comprises two hundred (200 µg) micrograms of BMA. The range of content recovery was eighty-five (85) percent of nominal drug content for the sirolimus and ninety-eight (98) percent of nominal drug content for cilostazol. The in vitro release kinetics for both cilostazol and sirolimus are illustrated in FIG. 4 and are described in more detail subsequently.

Figure 5:
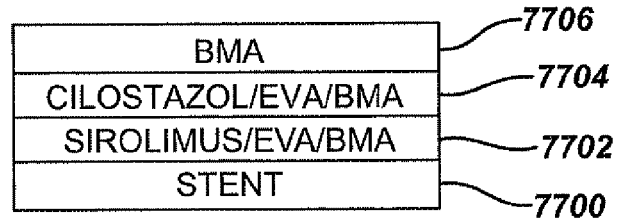
FIG. 5 is a diagrammatic representation of a second exemplary embodiment of a stent coated with a combination of sirolimus and cilostazol.

FIG. 5 illustrates a second exemplary configuration of a combination of cilostazol and a rapamycin on a stent. As described above, the stent is a Bx Velocity® stent available from Cordis Corporation. In this exemplary embodiment, the stent 7700 is coated with three layers. The first layer or inner layer 7702 comprises one hundred eighty (180 µg) micrograms of sirolimus which is equivalent to forty-five (45) percent by weight of the total weight of the inner layer 7702 and a copolymer matrix of EVA/BMA which is equivalent to fifty-five (55) percent by weight of the total weight of the inner layer 7702. The second layer or outer layer 7704 comprises one hundred (100 µg) micrograms of cilostazol which is equivalent to forty-five (45) percent by weight of the total weight of the outer layer 7704 and a copolymer matrix of EVA/BMA which is equivalent to fifty-five (55) percent by weight of the outer layer 7704. The third layer or diffusion overcoat 7706 comprises one hundred (100 µg) micrograms of BMA. Once again, the range of content recovery was eighty-five (85) percent of nominal drug content for the sirolimus and ninety-eight (98) percent of nominal drug content in cilostazol. The in-vitro release kinetics for both cilostazol and sirolimus are illustrated in FIG. 6 and are described in more detail subsequently.

Figure 4:
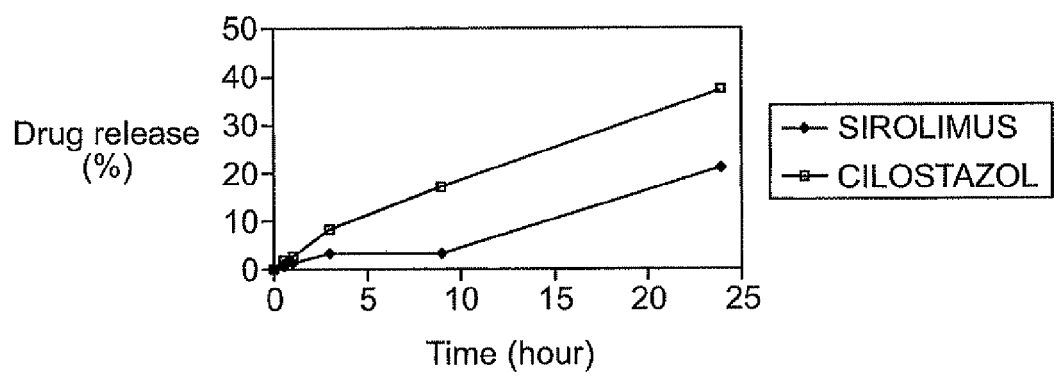
FIG. 4 is a graphical representation of the in vitro release kinetics of a first exemplary sirolimus and cilostazol combination stent.
Figure 6:
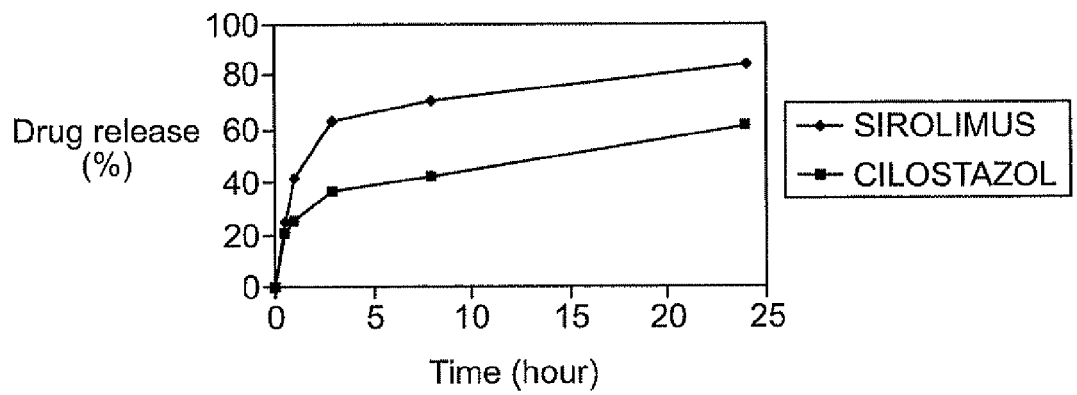
FIG. 6 is a graphical representation of the in vitro release kinetics of a second exemplary sirolimus and cilostazol combination stent coating.

As may be readily seen from a comparison of FIGS. 4 and 6, the drug release rate of both sirolimus and cilostazol was comparatively slower from the configuration comprising the thicker diffusion overcoat of BMA, i.e. two hundred micrograms rather than one hundred micrograms. Accordingly, additional control over the drug elution rates for both drugs may be achieved through the selective use of diffusion overcoats as described more fully herein. The selective use of diffusion overcoats includes thickness as well as other features, including chemical incompatibility.

Figure 7:
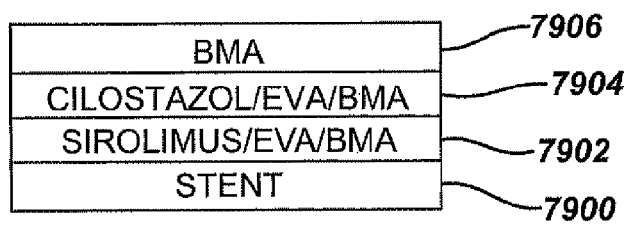
FIG. 7 is a diagrammatic representation of a third exemplary embodiment of a stent coated with a combination of sirolimus and cilostazol.

FIG. 7 illustrates a third exemplary configuration of a combination of cilostazol and a rapamycin on a stent. This configuration is identical in structure to that of the configuration of FIG. 3, but with the amount of cilostazol reduced to fifty (50 µg) micrograms. As with the previous exemplary embodiment, there is a stent 7900 and three additional layers 7902, 7904 and 7906. The percentage by weight, however, remains the same.

Figure 8:
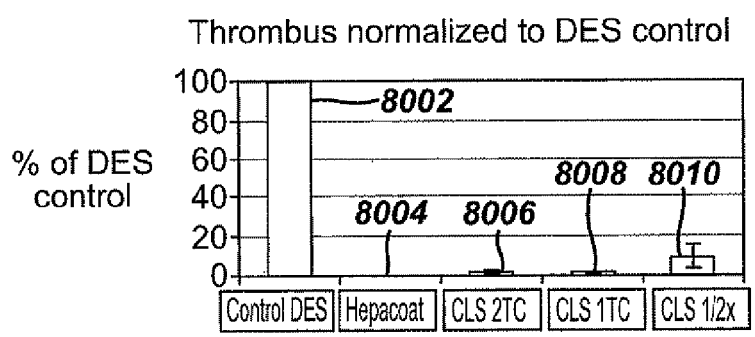
FIG. 8 is a graphical representation of the anti-thrombotic activity of a combination sirolimus and cilostazol drug eluting stent in an in vitro bovine blood loop model.

The anti-thrombotic efficacy of the above-described three configurations is illustrated in FIG. 8. FIG. 8 illustrates the anti-thrombotic properties of the sirolimus/cilostazol combination coatings described above in an in vitro bovine blood loop model. In the in vitro bovine blood loop model, fresh bovine blood is heparinized to adjust for acute clotting time (ACT) of about two hundred (200) seconds. The platelet content in the blood is labeled through the use of Indium 111. In the study, a stent is deployed in a silicone tube, which is part of a closed loop system for blood circulation. The heparinzed blood is circulated through the closed loop system by means of a circulating pump. Blood clots and thrombus builds up on a stent surface over time and reduces the flow rate of blood through the stented loop. The flow is stopped when the flow rate is reduced to fifty (50) percent of the starting value or at ninety (90) minutes if none of the tested stent reduces the flow by fifty (50) percent. The total radioactivity (In 111) on the stent surface is counted by a beta counter and normalized with the control unit, set as one hundred (100) percent in the chart. A smaller number indicates that the surface is less thrombogenic. All three sirolimus/cilostazol dual drug coating groups reduced platelet deposition and thrombus formation on the stent surface by more than ninety (90) percent compared to the control drug eluting stent without the additional cilostazol compound. Bar 8002 represents the control drug eluting stent which has been normalized to one hundred (100) percent. The control drug eluting stent is the Cypher® sirolimus eluting coronary stent available from Cordis Corporation. Bar 8004 is a stent coated with heparin and is available from Cordis Corporation under the HEPACOAT® on the Bx Velocity® coronary stent trademark. Bar 8006 is a stent configured as set forth with respect to the architecture illustrated in FIG. 3. Bar 8008 is a stent configured as set forth with respect to the architecture illustrated in FIG. 5. Bar 8010 is a stent configured as set forth with respect to the architecture illustrated in FIG. 7. As may be readily seen from FIG. 8, cilostazol significantly reduces thrombus formation.

Figure 9:
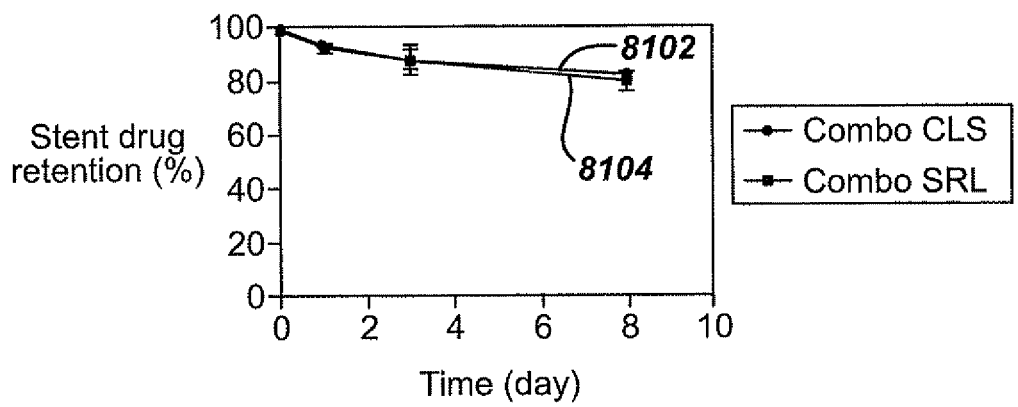
FIG. 9 is a graphical representation of the in vivo release kinetics of sirolimus and cilostazol from the stent illustrated in FIG. 11.
Figure 10:
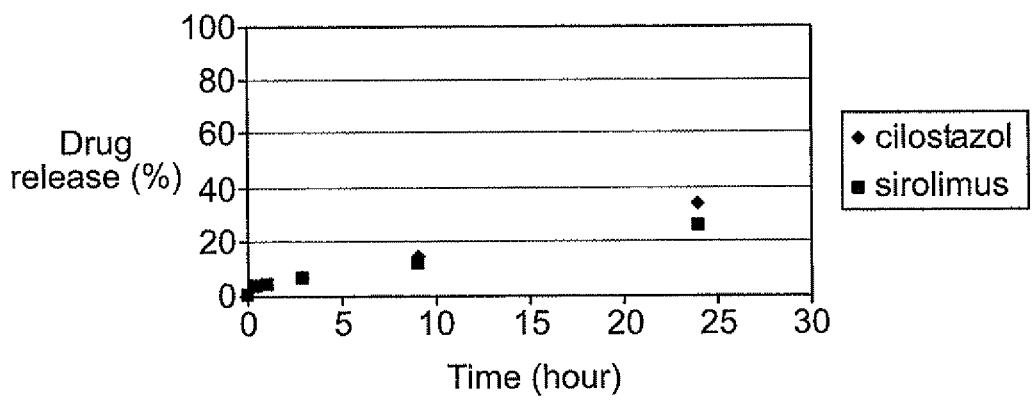
FIG. 10 is a graphical representation of the in vitro release kinetics of sirolimus and cilostazol from the stent illustrated in FIG. 11.
Figure 11:
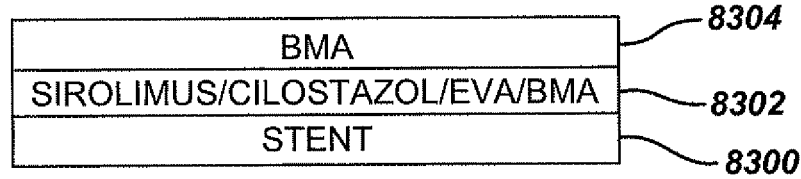
FIG. 11 is a diagrammatic representation of a fourth exemplary embodiment of a stent coated with a combination of sirolimus and cilostazol.

Another critical parameter for the performance of the thrombus resistance of a device coated with cilostazol is the duration of the drug release from the coating. This is of particular significance in the two weeks after device implantation. In the porcine drug elution PK studies of the dual drug eluting coating, both cilostazol and sirolimus were slowly released from the coating, resulting in a sustained drug release profile. The purpose of the porcine PK study is to assess the local pharmacokinetics of a drug eluting stent at a given implantation time. Normally three stents are implanted in three different coronary arteries in a pig for a given time point and then retrieved for total drug recovery analysis. The stents are retrieved at predetermined time points; namely, 1, 3 and 8 days. The stents are extracted and the total amount of drug remaining on the stents is determined by analysis utilizing HPLC (high performance liquid chromatography) for total drug amount. The difference between the original amount of drug on the stent and the amount of drug retrieved at a given time represents the amount of drug released in that period. The continuous release of drug into surrounding arterial tissue is what prevents the neointimal growth and restenosis in the coronary artery. A normal plot represents the percentage of total drug released (%, y-axis) vs. time of implantation (day, x-axis). As illustrated in FIG. 9, approximately eighty percent (80%) of the two drugs remained in the drug coating after eight (8) days of implantation. In addition, both drugs were released at a similar rate, despite the relatively large difference between their respective log P values and water solubility. Curve 8102 represents cilostazol and curve 8104 represents sirolimus. Their respective in vitro release profiles are illustrated in FIG. 10. Similar to the in vivo release profile, both sirolimus, represented by squares, and cilostazol, represented by diamonds, were released rather slowly, with only about thirty-five (35) percent release from both drugs. FIGS. 9 and 10 represent the in vivo and in vitro release rates from a stent coated in accordance with the configuration of FIG. 11 respectively, wherein the sirolimus and cilostazol are in one single layer, rather than in two separate layers. In this exemplary configuration, the stent 8300 is coated with two layers. The first layer 8302 comprises a combination of sirolimus, cilostazol and a copolymer matrix of EVA/BMA. The second layer or diffusion overcoat 8304 comprises only BMA. More specifically, in this embodiment, the first layer 8302 comprises a combination of sirolimus and cilostazol that is forty-five (45) percent by weight of the total weight of the first layer 8302 and an EVA/BMA copolymer matrix that is fifty-five (55) percent by weight of the total weight of the first layer 8302. The diffusion overcoat comprises one hundred (100 µg) micrograms of BMA.

Figure 12:
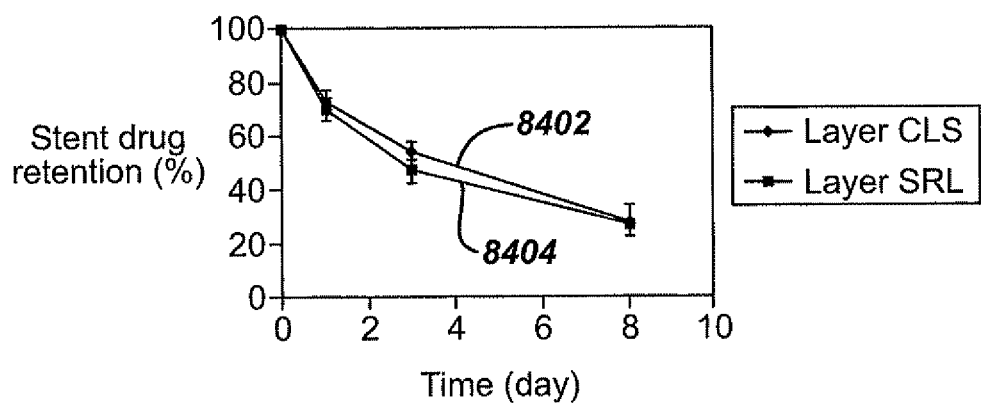
FIG. 12 is a graphical representation of the in vivo release kinetics of sirolimus and cilostazol from the stent illustrated in FIG. 3.
Figure 13:
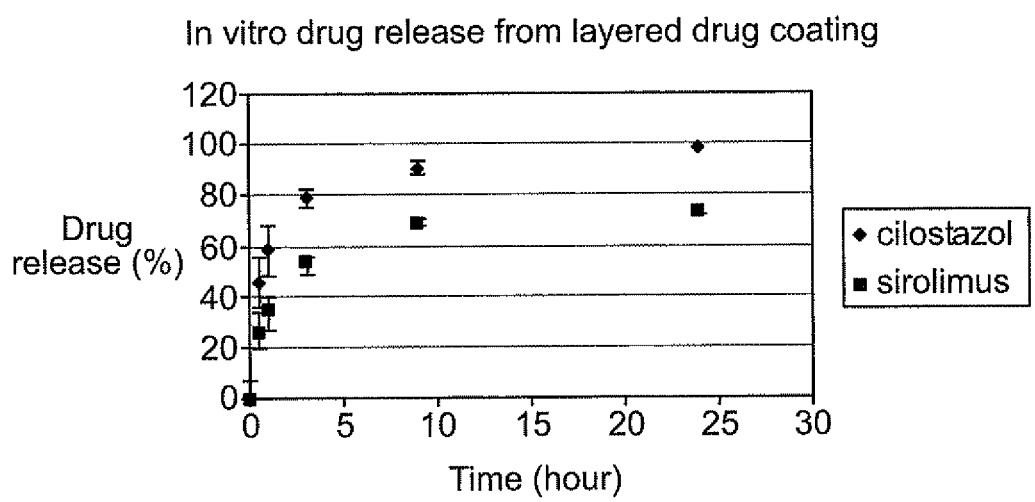
FIG. 13 is a graphical representation of the in vitro release kinetics of sirolimus and cilostazol from the stent illustrated in FIG. 3.

FIGS. 12 and 13 represent the in vivo and in vitro release rate from a stent coated in accordance with the configuration in FIG. 3, respectively. The layered dual drug eluting coating had a relatively faster release rate in the same porcine PK model compared to the dual drug base coating as may be readily seen from a comparison of FIGS. 12 and 9. In FIG. 12, curve 8402 represents the cilostazol and curve 8404 represents the sirolimus. However, the percentage release of both drugs were comparable at each time point. The respective in vitro release rate profiles are shown in FIG. 12, with the diamonds representing cilostazol and the squares representing sirolimus. In a comparison to the dual drug base coating, both drugs were released at a much faster rate, mirroring the fast release profiles shown in the in vivo PK study. Accordingly, combining the drugs in a single layer results in a higher degree of control over the elution rate.

The combination of a rapamycin, such as sirolimus, and cilostazol, as described above, may be more efficacious than either drug alone in reducing both smooth muscle cell proliferation and migration. In addition, as shown herein, cilostazol release from the combination coating may be controlled in a sustained fashion to achieve prolonged anti-platelet deposition and thrombosis formation on the stent surface or the surface of other blood contacting medical devices. The incorporation of cilostazol in the combination coating may be arranged in both a single layer with sirolimus or in a separate layer outside of the sirolimus containing layer. With its relatively low solubility in water, cilostazol has a potential to be retained in the coating for a relatively long period of time inside the body after deployment of the stent or other medical device. The relatively slow in vitro elution as compared to sirolimus in the inner layer suggests such a possibility. Cilostazol is stable, soluble in common organic solvents and is compatible with the various coating techniques described herein. It is also important to note that both sirolimus and cilostazol may be incorporated in a non-absorbable polymeric matrix or an absorbable matrix.

Figure 14:
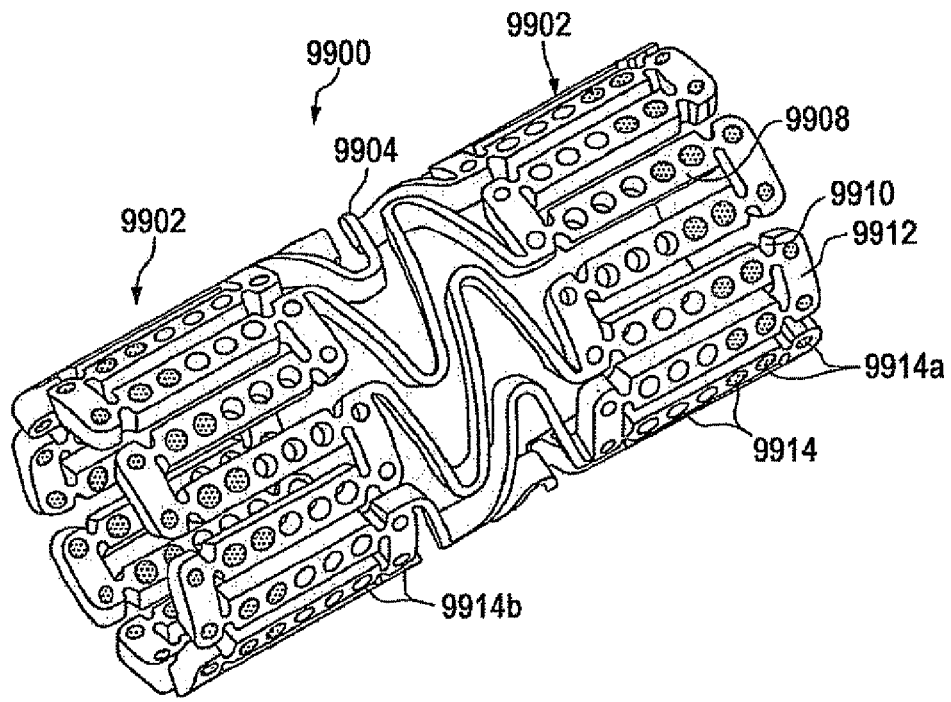
FIG. 14 is an isometric view of an expandable medical device with a beneficial agent at the ends thereof.

FIG. 14 illustrates an alternate exemplary expandable medical device having a plurality of holes containing a beneficial agent for delivery to tissue by the expandable medical device. The expandable medical device 9900 illustrated in FIG. 14 is cut from a tube of material to form a cylindrical expandable device. The expandable medical device 9900 includes a plurality of cylindrical sections 9902 interconnected by a plurality of bridging elements 9904. The bridging elements 9904 allow the tissue supporting device to bend axially when passing through the torturous path of vasculature to a deployment site and allow the device to bend axially when necessary to match the curvature of a lumen to be supported. Each of the cylindrical tubes 9902 is formed by a network of elongated struts 9908 which are interconnected by ductile hinges 9910 and circumferential struts 9912. During expansion of the medical device 9900 the ductile hinges 9910 deform while the struts 9908 are not deformed. Further details of one example of the expandable medical device are described in U.S. Pat. No. 6,241,762 which is incorporated herein by reference in its entirety.

As illustrated in FIG. 14, the elongated struts 9908 and circumferential struts 9912 include openings 9914, some of which contain a beneficial agent for delivery to the lumen in which the expandable medical device is implanted. In addition, other portions of the device 9900, such as the bridging elements 9904, may include openings, as discussed below with respect to FIG. 18. Preferably, the openings 9914 are provided in non-deforming portions of the device 9900, such as the struts 9908, so that the openings are non-deforming and the beneficial agent is delivered without risk of being fractured, expelled, or otherwise damaged during expansion of the device. A further description of one example of the manner in which the beneficial agent may be loaded within the openings 9914 is described in U.S. patent application Ser. No. 09/948,987, filed Sep. 7, 2001, which is incorporated herein by reference in its entirety.

The exemplary embodiments of the invention illustrated may be further refined by using Finite Element Analysis and other techniques to optimize the deployment of the beneficial agents within the openings 9914. Basically, the shape and location of the openings 9914, may be modified to maximize the volume of the voids while preserving the relatively high strength and rigidity of the struts with respect to the ductile hinges 9910. According to one preferred exemplary embodiment of the present invention, the openings have an area of at least $5\times10^{-6}$ square inches, and preferably at least $7\times10^{-6}$ square inches. Typically, the openings are filled about fifty percent to about ninety-five percent full of beneficial agent.

The various exemplary embodiments of the invention described herein provide different beneficial agents in different openings in the expandable device or beneficial agent in some openings and not in others. In other embodiments, combinations of beneficial agents or therapeutic agents may be utilized in single openings. The particular structure of the expandable medical device may be varied without departing from the spirit of the invention. Since each opening is filled independently, individual chemical compositions and pharmacokinetic properties may be imparted to the beneficial agent in each opening.

One example of the use of different beneficial agents in different openings in an expandable medical device or beneficial agents in some openings and not in others, is in addressing edge effect restenosis. As discussed herein, current generation coated stents may have a problem with edge effect restenosis or restenosis occurring just beyond the edges of the stent and progressing around the stent and into the interior luminal space.

The causes of edge effect restenosis in first generation drug delivery stents are currently not well understood. It may be that the region of tissue injury due to angioplasty and/or stent implantation extends beyond the diffusion range of current generation beneficial agents such as paclitaxel and rapamycin, which tend to partition strongly in tissue. A similar phenomenon has been observed in radiation therapies in which low doses of radiation at the edges of stent have proven stimulatory in the presence of an injury. In this case, radiating over a longer length until uninjured tissue is irradiated solved the problem. In the case of drug delivery stents, placing higher doses or higher concentrations of beneficial agents along the stent edges, placing different agents at the stent edges which diffuse more readily through the tissue, or placing different beneficial agents or combinations of beneficial agents at the edges of the device may help to remedy the edge effect restenosis problem.

FIG. 14 illustrates an expandable medical device 9900 with "hot ends" or beneficial agent provided in the openings 9914a at the ends of the device in order to treat and reduce edge effect restenosis. The remaining openings 9914b in the central portion of the device may be empty (as shown) or may contain a lower concentration of beneficial agent.

Other mechanisms of edge effect restenosis may involve cytotoxicity of particular drugs or combinations of drugs. Such mechanisms could include a physical or mechanical contraction of tissue similar to that seen in epidermal scar tissue formation, and the stent might prevent the contractile response within its own boundaries, but not beyond its edges. Further, the mechanism of this latter form of restenosis may be related to sequelae of sustained or local drug delivery to the arterial wall that is manifest even after the drug itself is no longer present in the wall. That is, the restenosis may be a response to a form of noxious injury related to the drug and/or the drug carrier. In this situation, it might be beneficial to exclude certain agents from the edges of the device.

Figure 15:
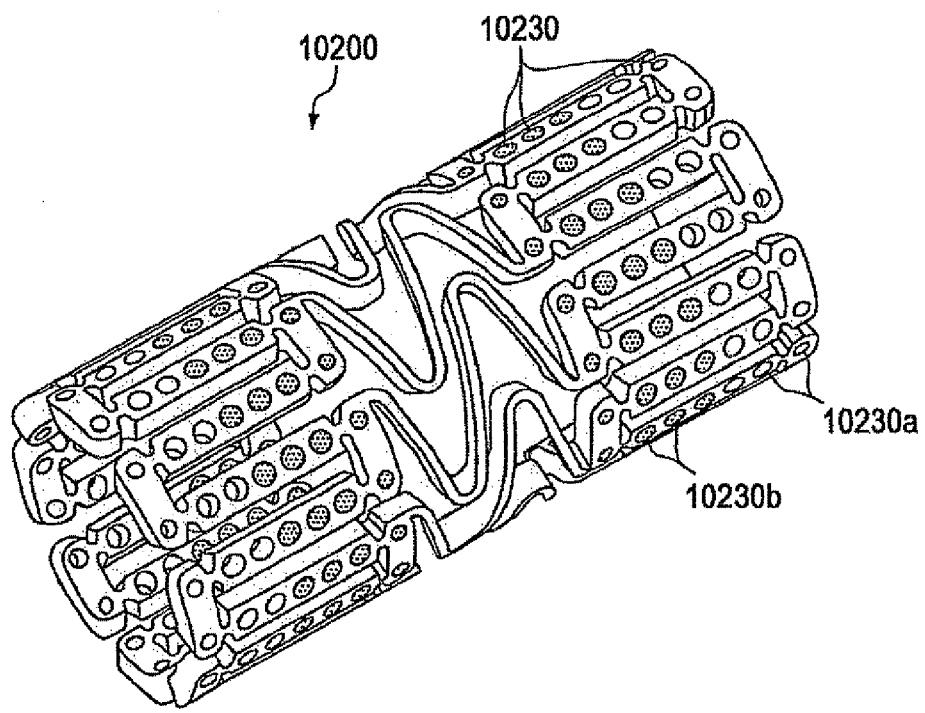
FIG. 15 is an isometric view of an expandable medical device with a beneficial agent at a central portion and no beneficial agent at the ends thereof.

FIG. 15 illustrates an alternate exemplary embodiment of an expandable medical device 10200 having a plurality of openings 10230 in which the openings 10230b in a central portion of the device are filled with a beneficial agent and the openings 10230a at the edges of the device remain empty. The device of FIG. 15 is referred to as having "cool ends."

In addition to use in reducing edge effect restenosis, the expandable medical device 10200 of FIG. 15 may be used in conjunction with the expandable medical device 9900 of FIG. 14 or another drug delivery stent when an initial stenting procedure has to be supplemented with an additional stent. For example, in some cases the device 9900 of FIG. 14 with "hot ends" or a device with uniform distribution of drug may be implanted improperly. If the physician determines that the device does not cover a sufficient portion of the lumen a supplemental device may be added at one end of the existing device and slightly overlapping the existing device. When the supplemental device is implanted, the device 10200 of FIG. 15 is used so that the "cool ends" of the medical device 10200 prevent double-dosing of the beneficial agent at the overlapping portions of the devices 9900, 10200.

Figure 16:
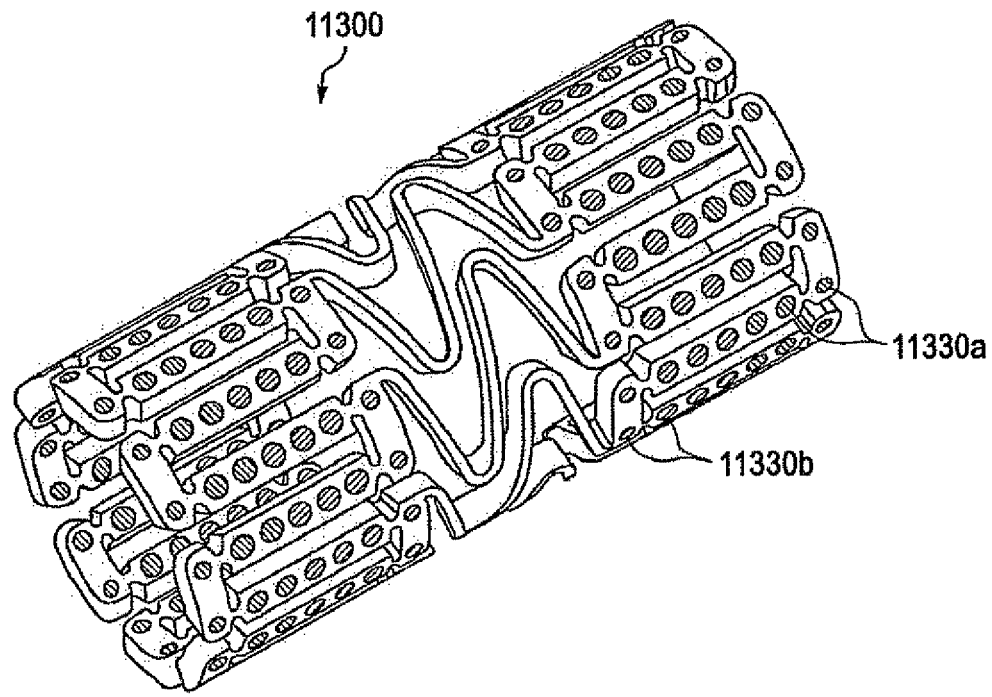
FIG. 16 is an isometric view of an expandable medical device with different beneficial agents in different holes.

FIG. 16 illustrates a further alternate exemplary embodiment of the invention in which different beneficial agents are positioned in different holes of an expandable medical device 11300. A first beneficial agent is provided in holes 11330a at the ends of the device and a second beneficial agent is provided in holes 11330b at a central portion of the device. The beneficial agent may contain different drugs, the same drugs in different concentrations, or different variations of the same drug. The exemplary embodiment of FIG. 16 may be used to provide an expandable medical device 11300 with either "hot ends" or "cool ends."

Preferably, each end portion of the device 11300 which includes the holes 11330a comprising the first beneficial agent extends at least one hole and up to about fifteen holes from the edge. This distance corresponds to about 0.005 to about 0.1 inches from the edge of an unexpanded device. The distance from the edge of the device 11300 which includes the first beneficial agent is preferably about one section, where a section is defined between the bridging elements.

Different beneficial agents comprising different drugs may be disposed in different openings in the stent. This allows the delivery of two or more beneficial agents from a single stent in any desired delivery pattern. Alternately, different beneficial agents comprising the same drug in different concentrations may be disposed in different openings. This allows the drug to be uniformly distributed to the tissue with a non-uniform device structure.

The two or more different beneficial agents provided in the devices described herein may comprise (1) different drugs; (2) different concentrations of the same drug; (3) the same drug with different release kinetics, i.e., different matrix erosion rates; or (4) different forms of the same drug. Examples of different beneficial agents formulated comprising the same drug with different release kinetics may use different carriers to achieve the elution profiles of different shapes. Some examples of different forms of the same drug include forms of a drug having varying hydrophilicity or lipophilicity.

In one example of the device 11300 of FIG. 16, the holes 11330a at the ends of the device are loaded with a first beneficial agent comprising a drug with a high lipophilicity while holes 11330b at a central portion of the device are loaded with a second beneficial agent comprising the drug with a lower lipophilicity. The first high lipophilicity beneficial agent at the "hot ends" will diffuse more readily into the surrounding tissue reducing the edge effect restenosis.

The device 11300 may have an abrupt transition line at which the beneficial agent changes from a first agent to a second agent. For example, all openings within 0.05 inches of the end of the device may comprise the first agent while the remaining openings comprise the second agent. Alternatively, the device may have a gradual transition between the first agent and the second agent. For example, a concentration of the drug in the openings may progressively increase (or decrease) toward the ends of the device. In another example, an amount of a first drug in the openings increases while an amount of a second drug in the openings decreases moving toward the ends of the device.

Figure 17:
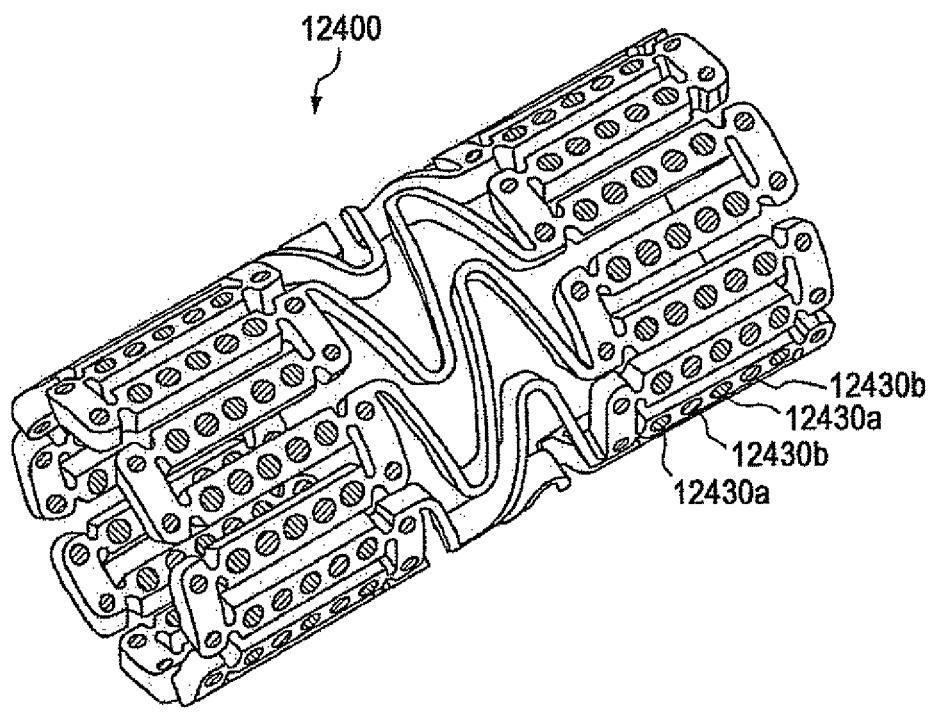
FIG. 17 is an isometric view of an expandable medical device with different beneficial agents in alternating holes.

FIG. 17 illustrates a further alternate exemplary embodiment of an expandable medical device 12400 in which different beneficial agents are positioned in different openings 12430a, 12430b in the device in an alternating or interspersed manner. In this manner, multiple beneficial agents may be delivered to tissue over the entire area or a portion of the area supported by the device. This exemplary embodiment will be useful for delivery of multiple beneficial agents where combination of the multiple agents into a single composition for loading in the device is not possible due to interactions or stability problems between the beneficial agents.

In addition to the use of different beneficial agents in different openings to achieve different drug concentrations at different defined areas of tissue, the loading of different beneficial agents in different openings may be used to provide a more even spatial distribution of the beneficial agent delivered in instances where the expandable medical device has a non-uniform distribution of openings in the expanded configuration.

The use of different drugs in different openings in an interspersed or alternating manner allows the delivery of two different drugs which may not be deliverable if combined within the same polymer/drug matrix composition. For example, the drugs themselves may interact in an undesirable way. Alternatively, the two drugs may not be compatible with the same polymers for formation of the matrix or with the same solvents for delivery of the polymer/drug matrix into the openings.

Further, the exemplary embodiment of FIG. 17 having different drugs in different openings in an interspersed arrangement provide the ability to deliver different drugs with very different desired release kinetics from the same medical device or stent and to optimize the release kinetic depending on the mechanism of action and properties of the individual agents. For example, the water solubility of an agent greatly affects the release of the agent from a polymer or other matrix. A highly water soluble compound will generally be delivered very quickly from a polymer matrix, whereas, a lipophilic agent will be delivered over a longer time period from the same matrix. Thus, if a hydrophilic agent and a lipophilic agent are to be delivered as a dual drug combination from a medical device, it is difficult to achieve a desired release profile for these two agents delivered from the same polymer matrix.

The system of FIG. 17 allows the delivery of a hydrophilic and a lipophilic drug easily from the same stent. Further, the system of FIG. 17 allows the delivery two agents at two different release kinetics and/or administration periods. Each of the initial release in the first twenty-four hours, the release rate following the first twenty-four hours, the total administration period and any other characteristics of the release of the two drugs may be independently controlled. For example the release rate of the first beneficial agent can be arranged to be delivered with at least forty percent (preferably at least fifty percent) of the drug delivered in the first twenty-four hours and the second beneficial agent may be arranged to be delivered with less than twenty percent (preferably less than ten percent) of the drug delivered in the first twenty-four hours. The administration period of the first beneficial agent may be about three weeks or less (preferably two weeks or less) and the administration period of the second beneficial agent may be about four weeks or more.

Restenosis or the recurrence of occlusion post-intervention, involves a combination or series of biological processes. These processes include the activation of platelets and macrophages. Cytokines and growth factors contribute to smooth muscle cell proliferation and upregulation of genes and metalloproteinases lead to cell growth, remodeling of extracellular matrix, and smooth muscle cell migration. A drug therapy which addresses a plurality of these processes by a combination of drugs may be the most successfully antirestenotic therapy. The invention provides a means to achieve such a successful combination drug therapy.

The examples discussed below illustrate some of the combined drug systems which benefit from the ability to release different drugs in different holes or openings. One example of a beneficial system for delivering two drugs from interspersed or alternating holes is the delivery of an anti-inflammatory agent or an immunosuppressant agent in combination with an antiproliferative agent or an anti-migratory agent. Other combinations of these agents may also be used to target multiple biological processes involved in restenosis. The anti-inflammatory agent mitigates the initial inflammatory response of the vessel to the angioplasty and stenting and is delivered at a high rate initially followed by a slower delivery over a time period of about two weeks to match the peak in the development of macrophages which stimulate the inflammatory response. The antiproliferative agent is delivered at a relatively even rate over a longer time period to reduce smooth muscle cell migration and proliferation.

In addition to the examples that are be given below, the following Table, Table 7.0, illustrates some of the useful two drug combination therapies which may be achieved by placing the drugs into different openings in the medical device.

other variations in device coverage which lead to uneven beneficial agent delivery concentrations, the concentration of the beneficial agent may be varied in the openings at portions of the device to achieve a more even distribution of the beneficial agent throughout the tissue. In the case of the exemplary embodiment illustrated in FIG. 18, the openings 13530*a* in the tube portions 13512 include a beneficial agent with a lower drug concentration than the openings 13530*b* in the bridging elements 13514. The uniformity of agent delivery may be achieved in a variety of manners including varying the drug concentration, the opening diameter or shape, the

TABLE 7.0

|  | PTX | 2-Cda | Epothilone D | Imatinib mesylate Gleevec | Rapamycin analog | Pimecrolimus | PKC-412 | Dexamethasone | Farglitazar | Insulin | VIP | ApoA-I milano |
|---|---|---|---|---|---|---|---|---|---|---|---|---|
| PTX |  | x |  | x |  | x | x | x |  | x | x | x |
| 2-CdA |  |  |  |  |  |  |  |  |  |  |  |  |
| Epothilone D |  |  | X | x | x | x | x |  | s |  |  |  |
| Imatinib Mesylate Gleevec |  |  |  | x |  |  | x | x |  | x | x | x |
| Rapamycin Analog |  |  |  |  | x | x | x | x |  |  |  |  |
| Pimecrolimus |  |  |  |  |  |  | x | x |  | x | x | x |
| PKC-412 |  |  |  |  |  |  | x | x |  | x | x | x |
| Dexamethasone |  |  |  |  |  |  |  | x |  | x | x | x |
| Farglitazar |  |  |  |  |  |  |  |  |  |  | x | x |
| Insulin |  |  |  |  |  |  |  |  |  |  | x | x |
| VIP |  |  |  |  |  |  |  |  |  |  | x |  |
| ApoA-I Milano |  |  |  |  |  |  |  |  |  |  |  | x |

The placement of the drugs in different openings allows the release kinetics to be tailored to the particular agent regardless of the hydrophobicity or lipophobicity of the drug. Examples of some arrangements for delivery of a lipophilic drug at a substantially constant or linear release rate are described in WO 04/110302 published on Dec. 23, 2004, which is incorporated herein by reference in its entirety. Examples of some of the arrangements for delivery of hydrophilic drug are described in WO 04/043510, published on May 27, 2004 which is incorporated herein by reference in its entirety. The hydrophilic drugs listed above include CdA, Gleevec, VIP, insulin, and ApoA-1 milano. The lipophilic drugs listed above include paclitaxel, Epothilone D, rapamycin, pimecrolimus, PKC-412 and Dexamethazone. Farglitazar is partly liphophillic and partly hydrophilic.

In addition to the delivery of multiple of drugs to address different biological processes involved in restenosis, the invention may deliver two different drugs for treatment of different diseases from the same stent. For example, a stent may deliver an anti-proliferative, such as paclitaxel or a limus drug from one set of openings for treatment of restenosis while delivering a myocardial preservative drug, such as insulin, from other openings for the treatment of acute myocardial infarction.

Figure 18:
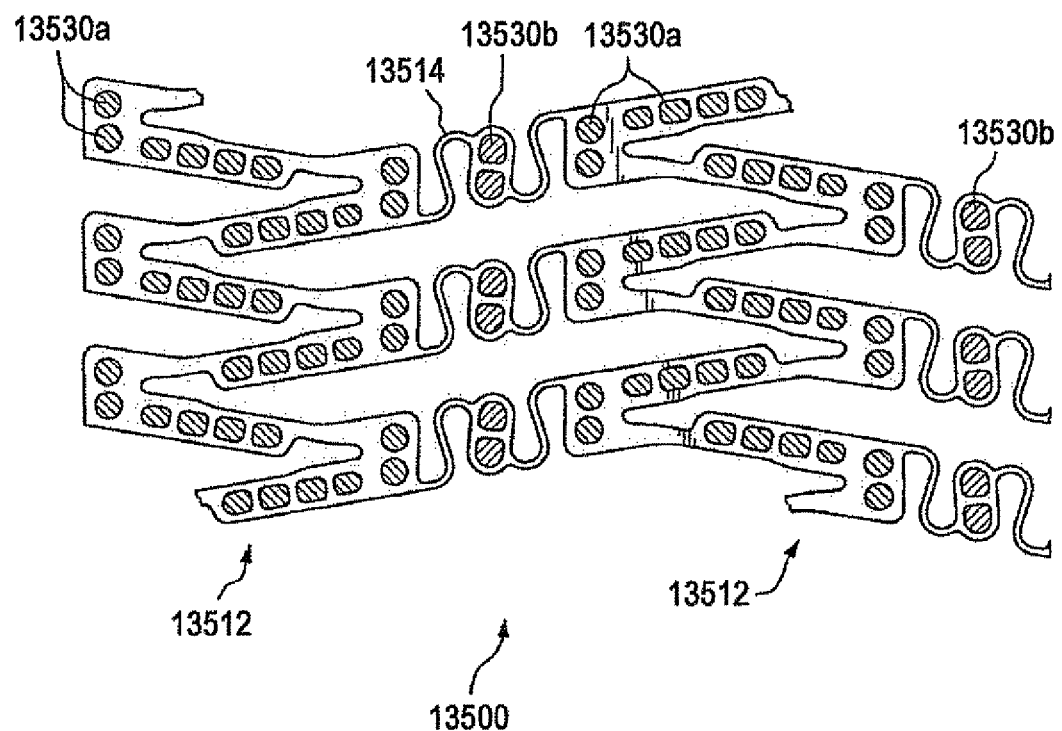
FIG. 18 is an enlarged side view of a portion of an expandable medical device with beneficial agent openings in the bridging elements.

In many of the known expandable devices and for the device illustrated in FIG. 18 the coverage of the device 13500 is greater at the cylindrical tube portions 13512 of the device than at the bridging elements 13514. Coverage is defined as the ratio of the device surface area to the area of the lumen in which the device is deployed. When a device with varying coverage is used to deliver a beneficial agent contained in openings in the device, the beneficial agent concentration delivered to the tissue adjacent the cylindrical tube portions 13512 is greater that the beneficial agent delivered to the tissue adjacent the bridging elements 13514. In order to address this longitudinal variation in device structure and amount of agent in the opening (i.e., the percentage of the opening filed), the matrix material, or the form of the drug.

Figure 19:
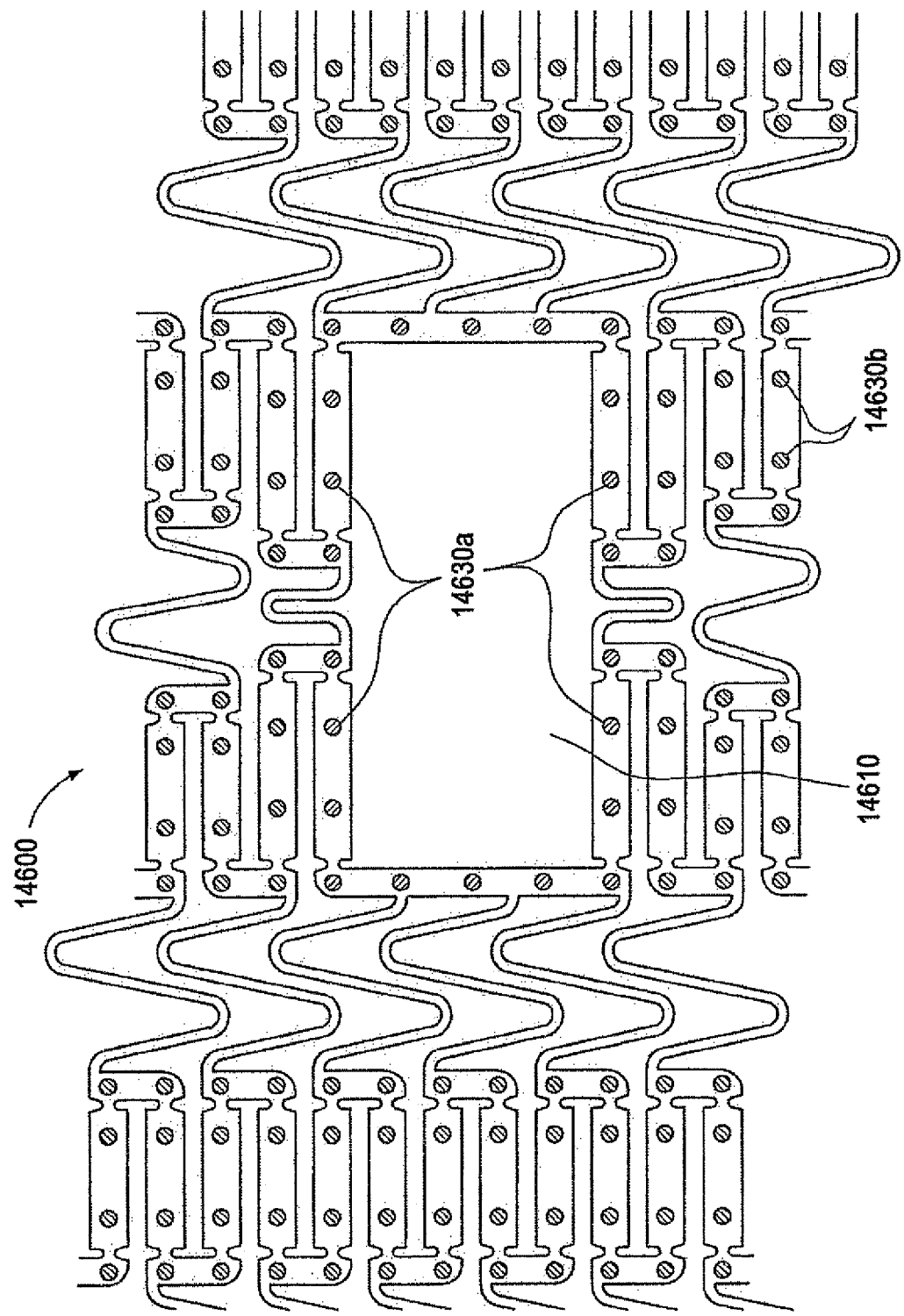
FIG. 19 is an enlarged side view of a portion of an expandable medical device with a bifurcation opening.

Another example of an application for the use of different beneficial agents in different openings is in an expandable medical device 14600, as illustrated in FIG. 19, configured for use at a bifurcation in a vessel. Bifurcation devices include a side hole 14610 which is positioned to allow blood flow through a side branch of a vessel. One example of a bifurcation device is described in U.S. Pat. No. 6,293,967 which is incorporated herein by reference in its entirety. The bifurcation device 14600 includes the side hole feature 14610 interrupting the regular pattern of beams which form a remainder of the device. Since an area around a bifurcation is a particularly problematic area for restenosis, a concentration of an antiproliferative drug may be increased in openings 14630*a* at an area surrounding the side hole 14610 of the device 14600 to deliver increased concentrations of the drug where needed. The remaining openings 14630*b* in an area away from the side opening contain a beneficial agent with a lower concentration of the antiproliferative. The increased antiproliferative delivered to the region surrounding the bifurcation hole may be provided by a different beneficial agent containing a different drug or a different beneficial agent containing a higher concentration of the same drug.

In addition to the delivery of different beneficial agents to the mural or abluminal side of the expandable medical device for treatment of the vessel wall, beneficial agents may be delivered to the luminal side of the expandable medical device to prevent or reduce thrombosis. Drugs which are delivered into the blood stream from the luminal side of the device may be located at a proximal end of the device or a distal end of the device.

The methods for loading different beneficial agents into different openings in an expandable medical device may include known techniques such as dipping and coating and also known piezoelectric micro-jetting techniques. Microinjection devices may be computer controlled to deliver precise amounts of two or more liquid beneficial agents to precise locations on the expandable medical device in a known manner. For example, a dual agent jetting device may deliver two agents simultaneously or sequentially into the openings. When the beneficial agents are loaded into through openings in the expandable medical device, a luminal side of the through openings may be blocked during loading by a resilient mandrel allowing the beneficial agents to be delivered in liquid form, such as with a solvent. The beneficial agents may also be loaded by manual injection devices.

Figure 20:
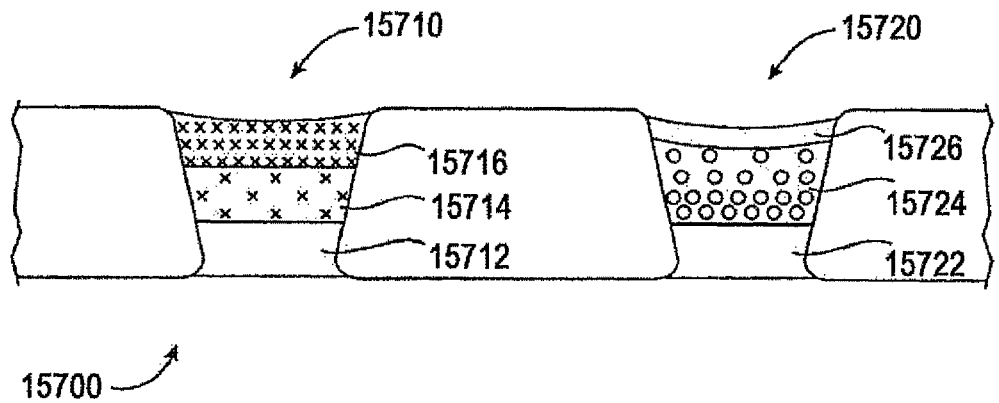
FIG. 20 is a cross sectional view of an expandable medical device having a combination of a first agent, such as an anti-inflammatory agent, in a first plurality of holes and a second agent, such as an anti-proliferative agent, in a second plurality of holes.

FIG. 20 illustrates a dual drug stent 15700 having an anti-inflammatory agent and an antiproliferative agent delivered from different holes in the stent to provide independent release kinetics of the two drugs which are specifically programmed to match the biological processes of restenosis. According to this example, the dual drug stent includes an anti-inflammatory agent pimecrolimus in a first set of openings 15710 in combination with the antiproliferative agent paclitaxel in a second set of openings 15720. Each agent is provided in a matrix material within the holes of the stent in a specific inlay arrangement designed to achieve the release kinetics illustrated in FIG. 21. Each of the drugs are delivered primarily murally for treatment of restenosis.

As illustrated in FIG. 20, pimecrolimus is provided in the stent for directional delivery to the mural side of the stent by the use of a barrier 15712 at the luminal side of the hole. The barrier 15712 is formed by a biodegradable polymer. The pimecrolimus is loaded within the holes in a manner which creates a release kinetics having dual phases. A first phase of the release of pimecrolimus is provided by a murally located region 15716 of the matrix which has a fast release formulation including pimecrolimus and biodegradable polymer (PLGA) with a high percentage of drug, such as about ninety percent drug to about ten percent polymer. A second phase of the release is provided by a central region 15714 of the matrix with pimecrolimus and biodegradable polymer (PLGA) in a ratio of about fifty percent drug to fifty percent polymer. As may be seen on the graph of FIG. 21, the first phase of the pimecrolimus release delivers about fifty percent of the loaded drug in about the first twenty-four hours. The second phase of the release delivers the remaining fifty percent over about two weeks. This release is specifically programmed to match the progression of the inflammatory process following angioplasty and stenting. In addition to or as an alternative to changing the drug concentration between the two regions to achieve the two phase release, different polymers or different comonomer ratios of the same polymer may be used in two drug different regions to achieve the two different release rates.

Figure 21:
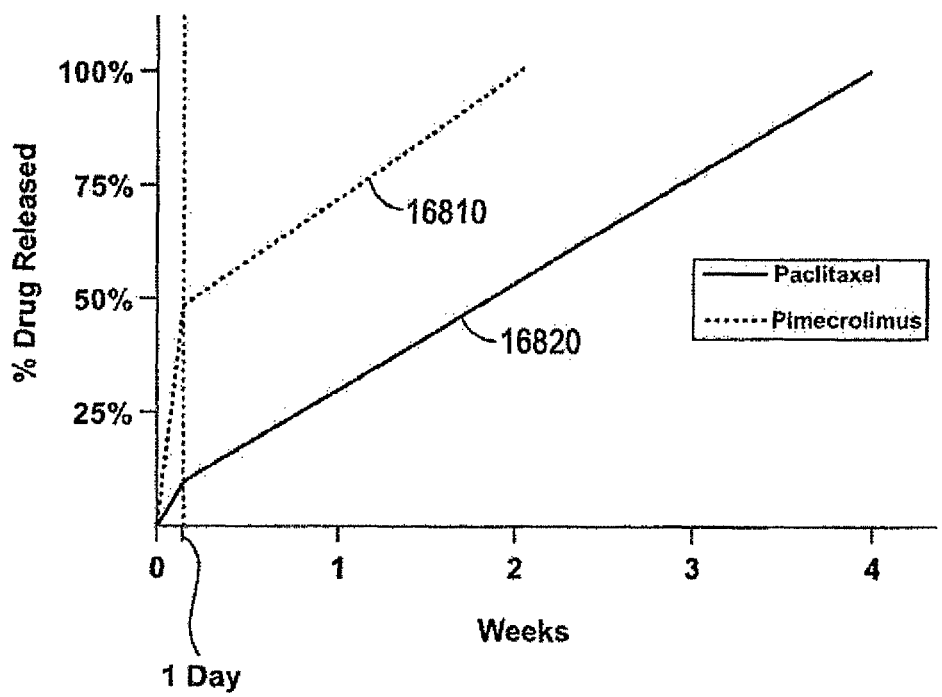
FIG. 21 is a graph of the release rates of one example of an anti-inflammatory and an anti-proliferative delivered by the expandable medical device of FIG. 20.

The paclitaxel is loaded within the openings 15720 in a manner which creates a release kinetic having a substantially linear release after the first approximately twenty-four hours, as illustrated in FIG. 21. The paclitaxel openings 15720 are loaded with three regions including a base region 15722 of primarily polymer with minimal drug at a luminal side of the hole, a central region 15724 with paclitaxel and polymer (PLGA) provided in a concentration gradient, and a cap region 15726 with primarily polymer which controls release of the paclitaxel. The paclitaxel is released with an initial release in the first day of about five to about fifteen percent of the total drug load followed by a substantially linear release for about twenty to ninety days. Additional examples of arrangements for paclitaxel in the holes with a concentration gradient are described in WO 04/110302 set forth above.

FIG. 20 illustrates the drug, barrier, and cap regions as distinct regions within the openings for ease of illustration. It should be understood that these regions indistinct and formed by a blending of the different areas. Thus, although the barrier layers are primarily polymer without drug, depending on the manufacturing processes employed, some small amount of drug of the subsequent region can be incorporation into the barrier region.

The amount of the drugs delivered varies depending on the size of the stent. For a three mm by six mm stent the amount of pimecrolimus is about fifty to about three micrograms preferably about one hundred to about two hundred fifty micrograms. The amount of paclitaxel delivered from this stent is about five to about fifty micrograms preferably about ten to about thirty micrograms. In one example, about two hundred micrograms of pimecrolimus and about twenty micrograms of paclitaxel are delivered. The drugs may be located in alternating holes in the stent. However, in view of the large difference in the doses to be delivered between the two drugs, it may be desirable to place the paclitaxel in every third of fourth hole in the stent. Alternatively, the holes for delivery of the low dose drug (paclitaxel) may be made smaller than the holes for the high dose.

The polymer/drug inlays are formed by computer controlled piezoelectric injection techniques as described in WO 04/026182 published on Apr. 1, 2004, which is incorporated herein by reference in its entirety. The inlays of the first agent may be formed first followed by the inlays of the second agent using the piezoelectric injector. Alternatively, the system of WO 04/02182 may be equipped with dual piezoelectric dispensers for dispensing the two agents at the same time.

According to this exemplary embodiment, the dual drug stent includes Gleevec in the first set of openings 15710 in combination with the antiproliferative agent paclitaxel in the second set of openings 15720. Each agent is provided in a matrix material within the holes of the stent in a specific inlay arrangement designed to achieve the release kinetics illustrated in FIG. 21.

The Gleevec is delivered with a two phase release including a high initial release in the first day and then a slow release for one to two weeks. The first phase of the Gleevec release delivers about fifty percent of the loaded drug in about the first twenty-four hours. The second phase of the release delivers the remaining fifty percent over about one-two weeks. The paclitaxel is loaded within the openings 15720 in a manner which creates a release kinetics having a substantially linear release after the first approximately twenty-four hours, as illustrated in FIG. 21 and as described above.

The amount of the drugs delivered varies depending on the size of the stent. For a three mm by six mm stent the amount of Gleevec is about two hundred to about five hundred micrograms, preferably about three hundred to about four hundred micrograms. The amount of paclitaxel delivered from this stent is about five to about fifty micrograms, preferably about ten to about thirty micrograms. As in the above described exemplary embodiment, the drugs may be located in alternating holes in the stent or interspersed in a non-alternating manner. The polymer/drug inlays are formed in the manner described above.

According to this exemplary embodiment, the dual drug stent includes PKC-412 (a cell growth regulator) in the first set of openings in combination with the antiproliferative agent paclitaxel in the second set of openings. Each agent is provided in a matrix material within the holes of the stent in a specific inlay arrangement designed to achieve the release kinetics discussed below.

The PKC-412 is delivered at a substantially constant release rate after the first approximately twenty-four hours, with the release over a period of about four to sixteen weeks, preferably about six to twelve weeks. The paclitaxel is loaded within the openings in a manner which creates a release kinetic having a substantially linear release after the first approximately twenty-four hours, with the release over a period of about four to sixteen weeks, preferably about six to twelve weeks.

The amount of the drugs delivered varies depending on the size of the stent. For a three mm by six mm stent the amount of PKC-412 is about one hundred to about four hundred micrograms, preferably about one hundred fifty to about two hundred fifty micrograms. The amount of paclitaxel delivered from this stent is about five to about fifty micrograms, preferably about ten to about thirty micrograms. As in the above-described exemplary embodiment, the drugs may be located in alternating holes in the stent or interspersed in a non-alternating manner. The polymer/drug inlays are formed in the manner described above.

Some of the agents described herein may be combined with additives which preserve their activity. For example additives including surfactants, antacids, antioxidants, and detergents may be used to minimize denaturation and aggregation of a protein drug. Anionic, cationic, or nonionic surfactants may be used. Examples of nonionic excipients include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEO) and polyvinyl pyrrolidone (PVP); carboxylic acids including D-lactic acid, glycolic acid, and propionic acid; surfactants with affinity for hydrophobic interfaces including n-dodecyl-.beta.-D-maltoside, n-octyl-.beta.-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; (PC) CM-PEG; cholic acid; sodium dodecyl sulfate (SDS); docusate (AOT); and taumocholic acid.

In accordance with another exemplary embodiment, a stent or intraluminal scaffold as described herein, may be coated with an anti-thrombotic agent in addition to one or more therapeutic agents deposited in the holes or openings. In one exemplary embodiment, the stent may be fabricated with the openings therein and prior to the addition or deposition of other therapeutic agents into the openings, an anti-thrombotic agent, with or without a carrier vehicle (polymer or polymeric matrix) may be affixed to the stent or a portion thereof. In this exemplary embodiment, the luminal and abluminal surfaces of the stent may be coated with the anti-thrombotic agent or coating, as well as the surfaces of the walls of the openings. In an alternative exemplary embodiment, a stent may first be coated with an anti-thrombotic agent or coating and then the openings may be fabricated. In this exemplary embodiment, only the luminal and abluminal surfaces would have the anti-thrombotic agent or coating and not the walls of the openings. In each of these embodiments any number of anti-thrombotic agents may be affixed to all or portions of the stents. In addition, any number of known techniques may be utilized to affix the anti-thrombotic agent to the stent such as that utilized with the HEPACOAT™ on the Bx Velocity® Coronary Stent from Cordis Corporation. Alternatively, the stents may be manufactured with a rough surface texture or have a micro-texture to enhance cell attachment and endothelialization, independently of or in addition to the anti-thrombotic coating. In addition, any number of therapeutic agents may be deposited into the openings and different agents may be utilized in different regions of the stent.

Referring now to FIGS. 22A, 22B and 22C, there is illustrated a diagrammatic representation of a portion of a stent.

As illustrated in FIG. 22A the stent 17900 comprises a plurality of substantially circular openings 17902. In this exemplary embodiment, the plurality of substantially circular openings 17902 extend through the wall of the stent 17900. In other words, the plurality of substantially circular openings 17902 extend from the abluminal surface of the stent 17904 to the abluminal surface of the stent 17906, wherein the wall thickness is defined as the distance between the luminal and abluminal surfaces. In other embodiments; however, the openings need not extend through the wall of the stent 17900. For example, the openings or reservoirs may extend partially from either the luminal or abluminal surfaces or both. The stent 17900 in FIG. 22A has untreated surfaces 17904 and 17906 and empty openings 17902.

In FIG. 22B, at least one surface has been coated with a therapeutic agent 17908. The therapeutic agent preferably comprises an anti-thrombotic agent such as heparin; however, any anti-thrombotic agent may be utilized. The anti-thrombotic agent may be affixed utilizing any technique as briefly described above. In this exemplary embodiment, both the abluminal and luminal surfaces have an anti-thrombotic agent affixed thereto. In addition, as there is nothing in the plurality of substantially circular openings 17902 at this juncture, the walls of the openings 17902 may also have some anti-thrombotic agent affixed thereto. The amount of anti-thrombotic agent affixed to the walls of the openings 17910 depends on how the agent is affixed. For example, if the agent is affixed by dip coating, the walls of the openings will have more agent affixed thereto than if the agent is affixed utilizing a spray coating technique. As described herein, in this exemplary embodiment, all exposed surfaces have a substantial anti-thrombotic coating affixed thereto; however, in alternate exemplary embodiments, only specific surfaces may have an anti-thrombotic affixed thereto. For example, in one exemplary embodiment, only the surface in contact with the blood may be treated with the anti-thromobotic agent. In yet another alternate exemplary embodiment, one or both surfaces may be coated with the anti-thrombotic agent while the walls of the openings are not. This may be accomplished in a number of ways including plugging the openings prior to coating or creating the openings after the anti-thrombotic agent is affixed.

FIG. 22C illustrates a completed stent in accordance with this exemplary embodiment. As illustrated in this figure, the plurality of substantially circular openings 17902 have been filled with one or more therapeutic agents for treating vascular diseases such as restenosis and inflammation or any other dieses as described herein. Each opening 17902 may be filled with the same therapeutic agent or different agents as described in detail above. As illustrated in the figure, these different agents 17912, 17914 and 17916 are used in a particular pattern; however, as detailed above, any combination is possible as well as utilizing a single agent with different concentrations. The drugs, such as a rapamycin, may be deposited in the openings 17902 in any suitable manner. Techniques for depositing the agent include micro-pippetting and/or ink-jet filling methods. In one exemplary embodiment, the drug filling may be done so that the drug and/or drug/polymer matrix in the opening will be below the level of the stent surfaces so that there is no contact with the surrounding tissue. Alternately, the openings may be filled so that the drug and/or drug/polymer matrix may contact the surrounding tissue. In addition, the total dose of each of the drugs, if multiple drugs are utilized, may be designed with maximal flexibility. Additionally, the release rate of each of the drugs may be controlled individually. For example, the openings near the ends may contain more drugs to treat edge restenosis.

In accordance with this exemplary embodiment, the hole or openings may be configured not only for the most efficacious drug therapy, but also for creating a physical separation between different drugs. This physical separation may aid in preventing the agents from interacting.

In accordance with another exemplary embodiment, a polymeric construct comprising a layer-by-layer arrangement of stereospecific polymers may be utilized as drug or therapeutic agent depot carriers or coatings for use in conjunction with medical devices. Medical devices as utilized herein means any of the devices described herein for local or regional drug delivery. Essentially, this polymeric construct may be utilized with any of the therapeutic agents or combinations thereof described herein, with any of the drug delivery devices described herein and with any of the implantable medical devices described herein. In addition, as intimated above, the polymeric construct may be utilized as a coating for coating some or all of the surfaces of an implantable medical device or as a carrier for filling reservoirs in implantable medical devices. The polymeric construct may take on any number of forms as is described in detail below.

In one exemplary embodiment the construct is formed from alternating layers of chemically identical, biodegradable polymers with different optical rotations. In this exemplary embodiment the biodegradable polymers are poly(D-lactic acid) (PDLA) and poly(L-lactic acid)(PLLA). Poly(D-lactic acid) is synthesized from stereo-specific RR-lactide dimer using a catalyst that maintains the chiral configurations during the ring-opening polymerization (ROP) process. Conversely, poly(L-lactic acid) is synthesized from SS-lactide dimer using a ROP process. The ROP conditions are known to those skilled also in the relevant art. These alternating layers in close proximity to one another form a sterocomplex that provides for superior results with respect to the local and regional drug and/or therapeutic agent delivery. In other words, the identical chemical properties of the two stereospecific polymers with variable physical properties enable a broad range of therapeutic agent stability and release controls. In addition, changes in the rheological properties of these sterocomplexed biodegradable polymers make these materials denser and lead to the use of a thinner coating thickness and potentially lower molecular weight polymer while achieving equal or better results than non-sterocomplexed polymers. These thinner coatings preferably should improve the long term biocompatibility of the coating and shorten the resorption time. Essentially, the layered poly(D-lactic acid) and poly(L-lactic acid) create sterocomplexes in situ that provide better control of therapeutic agent release pharmakinetics with a smaller amount of drug carrier matrix.

Figure 23A:
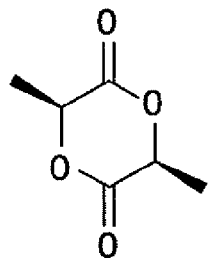
FIGS. 23A, 23B, 23C are exemplary lactide dimmers utilized in the synthesis of stereo-specific polylactides.
Figure 23B:
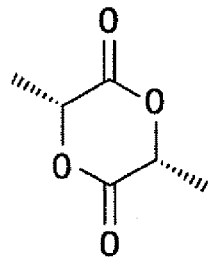
Figure 23C:
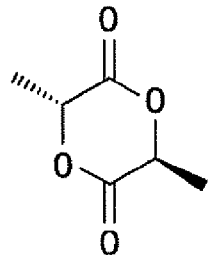

Polymer-polymer complexes may be formed upon the mixing of polymers of different chemical compositions under suitable conditions. These complexes include a polyelectrolyte complex between a polycation and a polyanion, a hydrogen bonding complex between a poly(carboxylic acid) and a polyether or polyol and a charge transfer complex between a polymeric donor and acceptor. However, only limited instances are known wherein a complex formation may occur between polymers of identical composition but different steric structures. The first such believed complex was observed by Ikada, Y., et al., Sterocomplex formation Between Enantiomeric poly(lactides), Marcomolecter, 1987, 20, 904-906, in 1987 between poly(L-lactic acid) and poly(D-lactic acid). It is known that polymers made from D, L-lactide are amorphous and optically inactive, while polymers made from L-lactide and D-lactide are partially crystalline and optically active. The L-lactide polymer is more crystalline than a D-lactide based polymer and may be more hydrophobic and thus degrade more slowly as a result. Ikada's study also demonstrated that when equal moles of poly(L-lactic acid) and poly(D-lactic acid) are mixed, the polymer blend has a single melting point of two-hundred thirty degrees C. which is higher than either of the individual melting points, approximately one hundred eighty degrees C. The crystalline structure of poly(L-lactide) made from SS-lactide as shown in FIG. 23A, consists of left-handed helical chains and poly(D-lactide), made from RR-lactide as shown in FIG. 23B, has a right-handed helical crystalline structure. FIG. 23C illustrates a meso-lactide which when polymerized results in an amorphous, racemic polymer.

Figure 24:
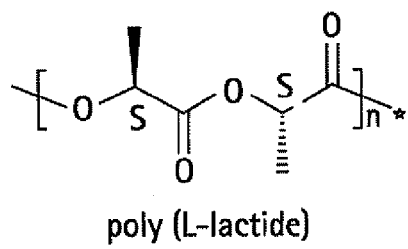
FIG. 24 illustrates a poly L-lactide.
Figure 25:
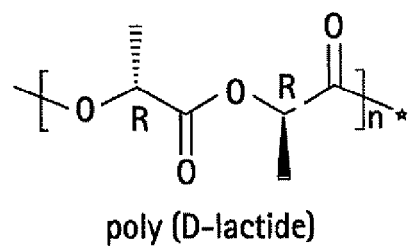
FIG. 25 illustrates a poly D-lactide.

The observations made by Ikada et al. may have significant implications when these lactide dimers are utilized in the synthesis of stereospecific polylactide as illustrated in FIGS. 24 poly(L-lactide) and 25 poly(D-lactide). It is for the reasons described herein that the sterocomplex formed between poly(D-lactic acid) and poly(L-lactic acid) may be more effective in providing a control over drug elution with comparatively smaller quantity of the carrier or thinner coating or optionally lower molecular weight. The sterocomplex formed between poly(D-lactic acid) and poly(L-lactic acid) may result in greater physical stability due to its resultant higher melting temperature and may also result in better storage of the therapeutic agent or agents contained therein. In addition, the lower molecular weight of the poly(D-lactic acid) and the poly(L-lactic acid) utilized in the serocomplex is likely to result in a shortened resorption time and better biocompatibility compared to the higher molecular weight individual polymers.

An exemplary process to take advantage of such sterocomplexes of poly(D-lactic acid) and poly(L-lactic acid) comprises mixing one of the stereospecific and optically pure polylactic acids with a therapeutic agent or combination of agents and coat at least a portion of the surface of a medical device using a common coating method such as spray coating. Any type of coating technique may be utilized such as those described herein. The next step involves mixing another stereospecific and optically pure polylactic acid with opposite optical rotation with a therapeutic agent or combination of agents and coating on top of the previous layer, optionally while the previous layer is still "wet." These polymers of opposite stereospecificity will bind in situ to form a sterocomplex and hold the therapeutic agent or combination of therapeutic agents in place for local or regional drug delivery. The process described above may be repeated any number of times until a proper level of therapeutic agent or combination of therapeutic agents is achieved. A top layer or coating of any of the two optically active polymers or a combination thereof may be applied to further regulate the release rate of the therapeutic agent or combination of agents from the coatings.

This process may be applied to at least a portion of the surface or surfaces of any of the medical devices described herein utilizing any of the therapeutic agents described herein, or combinations thereof, and utilizing any of the coating techniques described herein. In addition, the above described process may be utilized with or without therapeutic agents.

In an alternative exemplary embodiment, the therapeutic agents may be added after each layer is coated on the device rather than be mixed with the polymeric layers.

In yet another alternate exemplary embodiment, the combination of the optically pure polylactides and/or therapeutic agents described above may be mixed and deposited into a receptacle, for example, a well, inside of a medical device to accomplish the layer-by-layer therapeutic agent leading configuration.

Figure 26A:
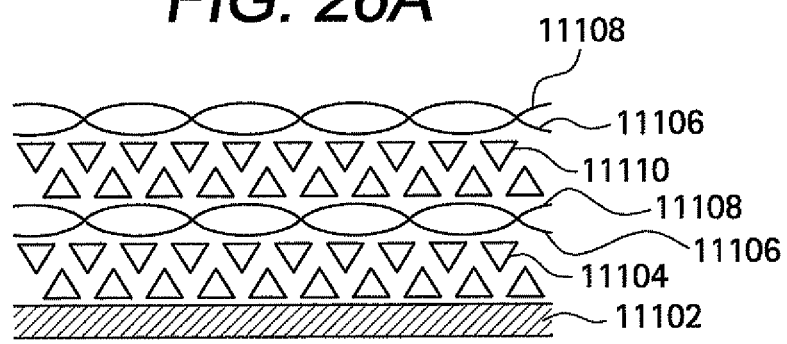
FIGS. 26A, 26B and 26C illustrate coating or deposition schemes utilizing alternating layer-by-layer polymers having identical chemical compositions but with different optical rotations with therapeutic agents.
Figure 26B:
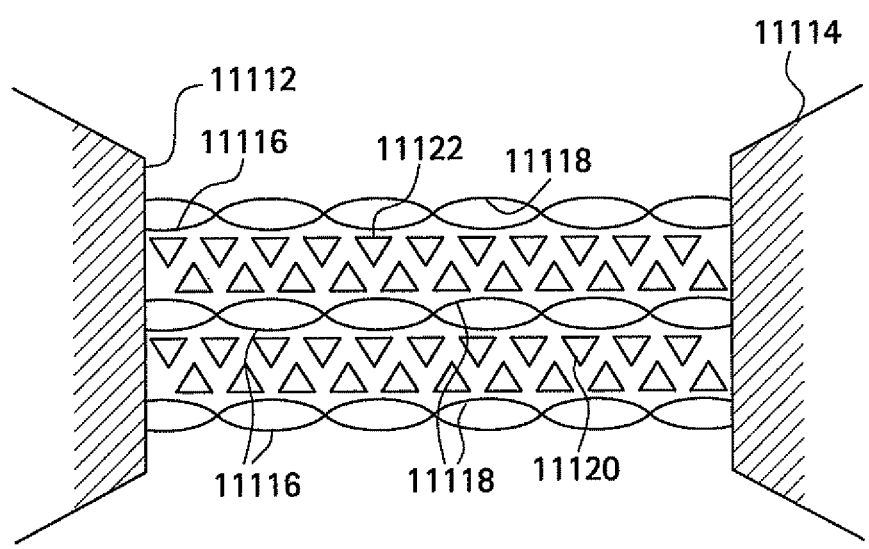
Figure 26C:
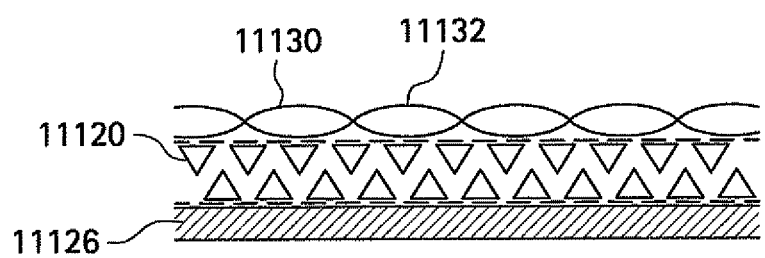

Referring to FIGS. 26A, 26B and 26C, there is illustrated the exemplary coating or deposition scheme utilizing an alternating layer-by-layer of poly(D-lactic acid) and poly(L-lactic acid) optionally with a therapeutic agent or agents interspersed therebetween. Specifically, in FIG. 26A there is illustrated a section 11102 of a medical device having the layer-by-layer sterocomplexed coating thereon. In this exemplary embodiment, one or more first therapeutic agents 11104 is mixed with poly(D-lactic acid) 11106 and affixed to the surface of the section 11102 of the medical device. A second layer comprising poly(L-lactic acid) 11108 is affixed to the first layer thereby forming the basic building block of the layer-by-layer construct. It is important to note that additional layers may be utilized, with the same or different therapeutic agents 1110 so long as chemically identical, but physically different polymers were utilized. As illustrated, one or more additional therapeutic agents 11110 are affixed to the polymer building block layer and then a second polymer building block layer comprising poly(D-lactic acid) 11106 and poly(L-lactic acid) 11108 is affixed thereto.

FIG. 26B illustrates a reservoir 11112 in a section 11114 of a medical device having the layer-by-layer sterocomplexed coating deposited therein. In this exemplary embodiment, a first bottom barrier layer consisting of poly(D-lactic acid) 11116 and poly(L-lactic acid) 11118 is laid down by a standard deposition method such as ink-jetting. Poly(D-lactic acid) and poly(L-lactic acid) may be pre-mixed in a common solvent and deposited into the reservoir, deposited sequentially to form the stereopcomplex barrier layer. The amount of poly(D-lactic acid) and poly(L-lactic acid) is preferably substantially the same. Subsequently poly(D-lactic acid) 11116 mixed with a therapeutic agent 11120 or combinations of therapeutic agents 11120 are deposited in the reservoir, followed by deposition of poly(D-lactic acid) 11118 to form in situ stereocomplex and drug polymer matrix. A second layer of stereocomplex of poly(D-lactic acid) and poly(L-lactic acid), optionally mixed with the same or different therapeutic agent 11122 may be deposited on the first layer, forming the layer-by-layer construct once again. Such alternating layers may be repeated for a number of times. Optional top barrier layers comprising poly(D-lactic acid) and poly(L-lactic acid) 1118 may be deposited to regulate drug release from the top side of the reservoir.

As set forth above, the therapeutic agent or agents may be mixed with the polymers or just deposited or coated in between the polymers.

FIG. 26C illustrates a layer-by-layer deposition of poly(D-lactic acid) 11130 and poly(L-lactic acid) 11132 utilized as a drug diffusion barrier for a therapeutic agent or combination of agents 11128 on the surface of a section 11126 of a medical device.

Figure 27A:
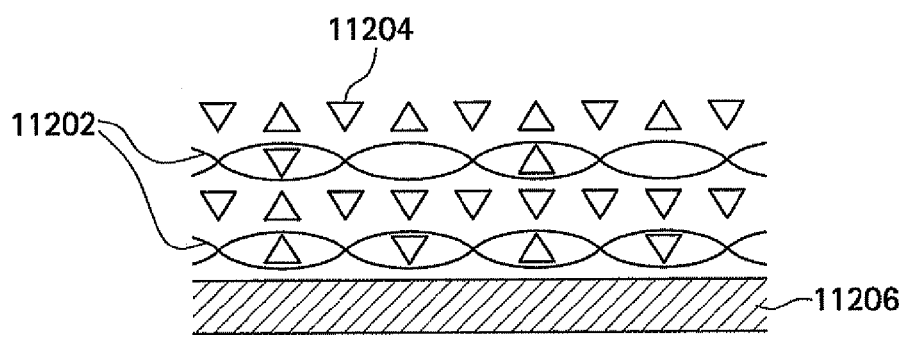
FIGS. 27A, 27B illustrate coating or deposition schemes utilizing solutions containing both poly(D-lactic acid) and poly(L-lactic acid) at a substantially one-to-one molar ratio.
Figure 27B:
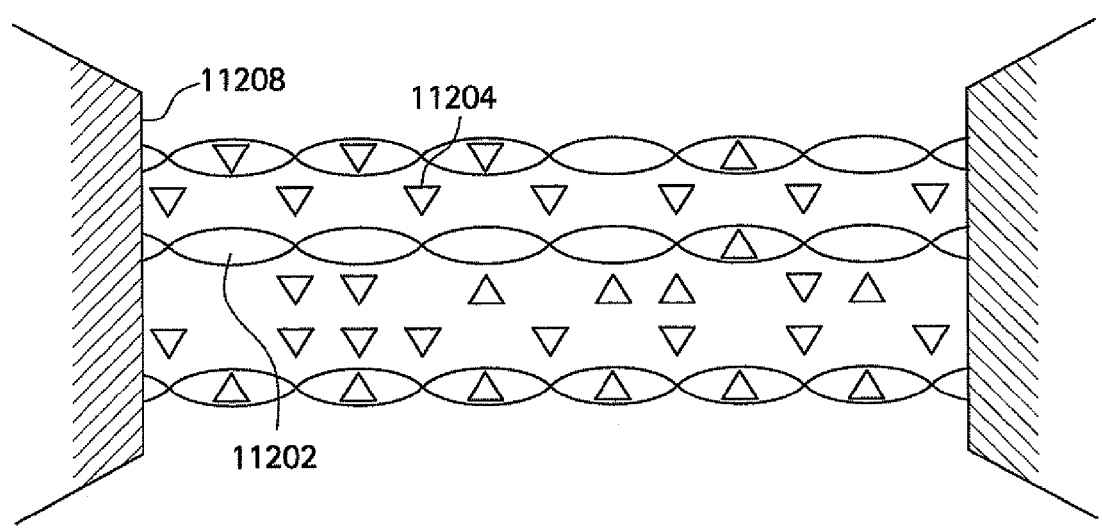

FIGS. 27A and 27B illustrate a coating or deposition scheme utilizing polymer solutions 11202 comprising both poly(D-lactic acid) and poly(L-lactic acid) at a substantially one to one molar ratio, optionally with a therapeutic agent or agents 11204 dispersed within the solution and affixed to a surface 11206 of a device or deposited in a reservoir 11208 of a device.

In accordance with another exemplary embodiment, the present invention is directed to a vascular dual drug eluting stent having reservoirs, as described above, wherein a portion of these reservoirs comprise a composition that releases sirolimus (a rapamycin) predominantly in the mural or abluminal direction, and a complimentary portion of these reservoirs comprise a composition that releases cilostazol predominantly in the luminal direction. More specifically, when the dual drug eluting stent is positioned in an artery of a patient, the sirolimus will elute locally into the arterial tissue and treat and mitigate restenosis in the artery while the cilostazol will elute into the bloodstream and provide an anti-thrombotic effect within the lumen of the dual drug eluting stent and the local arterial wall adjacent to the drug eluting stent. The anti-thrombotic effect is two-fold; namely, the mitigation of thrombus formation on or near the implanted dual drug eluting stent, and the inhibition of platelet aggregation and deposition on or near the dual drug eluting stent. In addition, when the dual drug eluting stent is utilized in the treatment of a patient suffering from an acute myocardial infarction, the cilostazol may provide a cardio protective effect to the myocardial tissue supplied with blood by the treated artery, such as by limiting a "no reflow" condition after stenting, by mitigating reperfusion injury and/or by reducing infarct size. The dual drug eluting stent may also improve clinical outcomes for patients with poor healing characteristics, such as patients with diabetes.

In this exemplary embodiment of the dual drug eluting stent, the reservoirs are utilized to directionally deliver two different therapeutic agents or drugs from the stent. A composition of a polymer and sirolimus provides for the controlled, sustained local delivery of the sirolimus from a portion of the reservoirs of the stent abluminally to the arterial tissue of the patient. A composition of a polymer and cilostazol provides for the controlled, sustained delivery of cilostazol luminally from different and separate reservoirs of the stent either directly into the blood stream of the artery under treatment, or at a later time after stent implantation into the biologic tissue that grows to cover the luminal surface of the stent.

It is important to note that although separate and distinct reservoirs are described herein, any other suitable directional delivery mechanism may be utilized.

Figure 28:
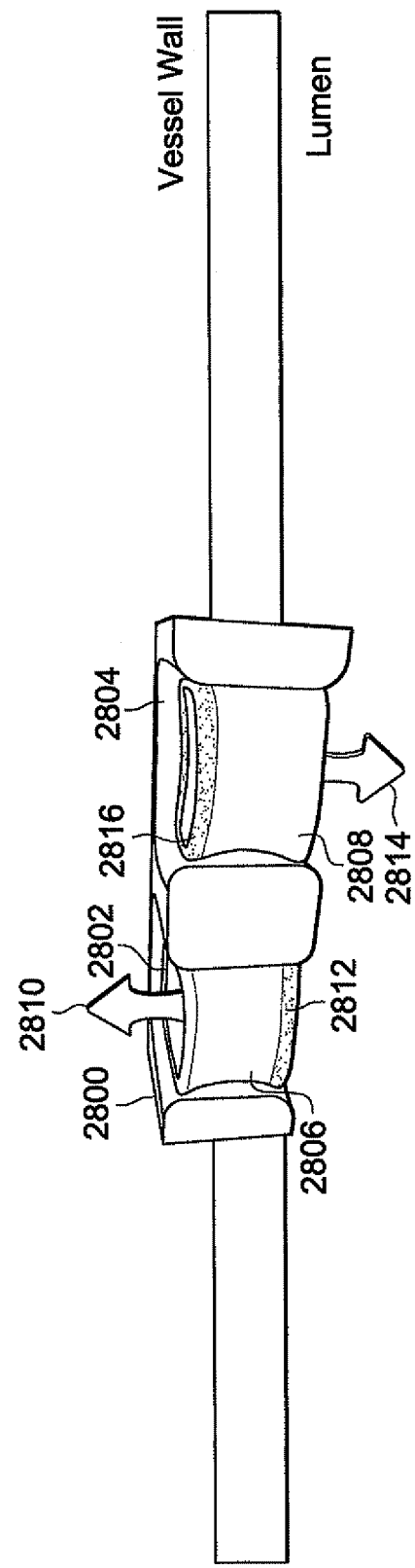
FIG. 28 is a diagrammatic, side view representation of a portion of a dual drug eluting stent.

FIG. 28 is a diagrammatic, side view representation of a portion of a dual drug eluting stent in accordance with the invention. Although the pattern for therapeutic agent or drug delivery may be tailored for a number of different situations or treatment scenarios, for ease of explanation adjacent reservoirs are described as comprising the different drugs. The dual drug eluting stent 2800 is illustrated comprising two reservoirs 2802 and 2804, one being filled with a sirolimus composition 2806 and the other being filled with a cilostazol composition 2808.

The sirolimus composition comprises sirolimus and a PLGA matrix. In the exemplary embodiment, 162 micrograms of sirolimus is mixed with 93 micrograms of PLGA. The mixing and reservoir filling process is described in detail below. To ensure a majority of the sirolimus is released to the mural or abluminal side of the dual drug stent 2800 as indicated by arrow 2810, a base structure 2812 is utilized as a plug in the opening of the reservoir 2802 on the luminal side. This base structure 2812 may comprise any suitable biocompatible material. In the exemplary embodiment, the base structure 2812 comprises PLGA. The formation of the base structure 2812 is described in detail subsequently.

The cilostazol composition comprises cilostazol and a PLGA matrix. In the exemplary embodiment, 120 micrograms of cilostazol is mixed with 120 micrograms of PLGA. The mixing and reservoir filling process is described in detail below. To ensure a majority of the cilostazol is released to the luminal side of the dual drug stent 2800 as indicated by arrow 2814, a cap structure 2816 is utilized as a plug in the opening of the reservoir 2804 on the abluminal side. This cap structure 2816 may comprise any suitable biocompatible material. In the exemplary embodiment, the cap structure 2816 comprises PLGA. The formation of the cap structure 2816 is described in detail subsequently.

The drug and polymer amounts set forth above are totals for a 3.5 millimeter by 17 millimeter size stent. The dosage ranges for each drug are described in detail subsequently. In addition, the polymer weight is the sum of the polymer in the matrix plus the polymer in the base or cap structure. The amount of polymer utilized is also explained in detail subsequently.

As described above, the reservoirs of the stent may be filled or loaded in any number of ways. In the exemplary embodiment, the compositions are filled or filled into the reservoir wells or reservoirs in two separate and sequential series of steps, including firstly depositing a fluid filling solution composition into the reservoirs and secondly evaporating the majority, if not substantially all, of the filling solution solvent. Having no solvent in the final composition is the ideal situation. The compositions in accordance with the present invention as described above are the solid materials that remain in the reservoirs after removal of substantially all and preferably all of the solvent from the filling solution composition.

The fluid compositions used to form the solid composition comprising sirolimus include a bioresorbable or bioabsorbable polymer, preferably a poly(lactide-co-glycolide) (PLGA) polymer, a suitable solvent such as dimethyl sulfoxide, DMSO, or N-methyl pyrrolidinone, NMP, sirolimus and optionally a stabilizer or anti-oxidant such as BHT. Preferably, at least one of the fluid filling solution compositions utilized in a deposition step to create the final sirolimus composition in the stent reservoir comprises BHT. Alternatives for BHT include butylated hydroxyl anisole, BHA, gallate esters such as propyl gallate or ascorbates esters such as palmitoyl ascorbate. BHT is preferred based upon its high level of effectiveness in stabilizing sirolimus, its low toxicity and its hyrophobiticity. BHT elutes from the reservoirs at approximately the same rate as sirolimus so there is always BHT present with the sirolimus. Alternatives for DMSO and NMP include dimethyl acetomide (DMAc) or dimethyl formamide (DMF). DMSO is preferred because sirolimus is more stable in the presence of DMSO.

Each sequential fluid composition that is deposited may comprise the same ingredients, or sequential filling solutions may be prepared from filling solutions comprising different ingredients. Preferably, the first series of filling solution deposits comprise only polymer and solvent, which are dried after each filling step. This part of the process results in the formation or construct of the base structure 2812. Once the base structure 2812 is formed, subsequent solutions comprising polymer, solvent, sirolimus and preferably BHT are added and which are also dried after each filling step. This manufacturing sequence will create a reservoir composition in which there is a lower concentration of sirolimus in the area of the luminal face of the reservoir and a relatively higher concentration of sirolimus in the area of the mural face of each reservoir. Such a configuration, as described in detail above, creates a longer path or higher resistance to elution of the drug to the luminal face as compared to the mural face and as such should result in substantially all of the sirolimus being delivered to the mural side of the stent and into the arterial tissue. In other words, the portion of reservoirs that deliver sirolimus in a predominantly mural direction will have a design where the volume of the reservoir on and near the luminal surface of the stent will be comprised predominantly of polymer and a minor amount of sirolimus, while the volume of the same reservoir at or near the mural surface will be comprised predominantly of sirolimus with a minor proportion of polymer.

The sirolimus composition within a reservoir will preferably comprise sirolimus, a bioresorbable polymer, a stabilizing agent and a solvent, and be in certain proportions to one another. Preferably, the total dose or amount of sirolimus available from the drug eluting stent is between 0.6 and 3.2 micrograms per square millimeter of arterial tissue area, where the area of arterial tissue is defined as the area of the surface of a theoretical cylinder whose diameter and length are the diameter and length of the expanded stent as deployed in the artery. More preferably, the total dose or amount of sirolimus available from the drug eluting stent is between 0.78 and 1.05 micrograms per square millimeter of arterial tissue.

As set forth above, the bioresorbable polymer utilized in the composition comprises PLGA. More preferably, the composition comprises a PLGA polymer where the molar ratio of lactide to glycolide residues (L:G) in the polymer chain is from about 85:15 to about 65:35. Even more preferably, the composition comprises a PLGA polymer where the molar ratio of lactide to glycolide residues (L:G) in the polymer chain is from about 80:20 to about 70:30. The PLGA should preferably have an intrinsic viscosity in the range from about 0.3 to about 0.9. Even more preferably, the PLGA should have an intrinsic viscosity in the range from about 0.6 to about 0.7. The weight ratio of sirolimus to PLGA, designated as the D/P ratio, is preferably in the range from about 50/50 to about 70/30, and more preferably from about 54/46 to about 66/34. All ratios are weight percentages. Alternatively, the relative weight proportions of sirolimus and PLGA may be expressed in a normalized form, D:P. Accordingly, the preferred D:P ration is in the range from about 1:0.4 to about 1:1.2 and more preferably from about 1:0.52 to about 1:0.85.

Also as described above, the sirolimus composition preferably comprises BHT, butylated hydroxyl toluene. The amount of BHT added is preferably in the range from about 1 percent by weight to about 3 percent by weight of the amount of sirolimus. Even more preferably, the amount of BHT added is in the range from about 1.2 percent by weight to about 2.6 percent by weight of the amount of sirolimus.

In order to make the above-described constituents a solution for filling purposes, a suitable solvent is required. Dimethyl sulfoxide, DMSO, is the preferred solvent and is preferably utilized in an amount in the range from about 1 percent to about 20 percent by weight relative to the weight of sirolimus. Even more preferably DMSO is utilized in an amount in the range from about 1 percent to about 15 percent by weight relative to the weight of sirolimus. Even yet more preferably DMSO is utilized in an amount in the range from about 4 percent to about 12 percent by weight relative to the weight of sirolimus.

The fluid compositions used to form the solid composition comprising cilostazol include a bioresorbable or bioabsorbable polymer, preferably a poly(lactide-co-glycolide), PLGA, polymer, a suitable solvent such as DMSO or NMP and cilostazol. The same alternatives for DMSO and NMP may be utilized in this composition, but once again DMSO is preferred.

Each sequential fluid composition that is deposited may comprise the same ingredients, or sequential filling solutions may be prepared from filling solutions comprising different ingredients. Preferably, the first series of filling solution deposits comprise polymer, cilostazol and solvent, which are dried after each filling step and the last series of filling solutions, comprise just polymer and solvent, which are also dried after each filling step. This process results in the formation or construct of the cap structure 2816. This manufacturing sequence will create a reservoir composition in which there is a lower concentration of cilostazol in the area of the mural face of the reservoir and a relatively higher concentration of cilostazol in the area of the luminal face of each reservoir. Such a configuration, as described in detail above, creates a longer path or higher resistance to elution of the drug to the mural face as compared to the luminal face and as such should result in substantially all of the cilostazol being delivered to the luminal side of the stent and into the bloodstream and/or arterial tissues. In other words, the portion of reservoirs that deliver cilostazol in a predominantly luminal direction will have a design where the volume of the reservoir on and near the mural surface of the stent will be comprised predominantly of polymer and a minor amount of cilostazol, while the volume of the same reservoir at or near the luminal surface will be comprised predominantly of cilostazol with a minor proportion of polymer.

The cilostazol composition within a reservoir will preferably comprise cilostazol, a bioresorbable polymer and a solvent, and be in certain proportions to one another. Preferably, the total dose or amount of cilostazol available from the drug eluting stent is between 0.4 and 2.5 micrograms per square millimeter of arterial tissue area, where the area of arterial tissue is defined as the area of the surface of a theoretical cylinder whose diameter and length are the diameter and length of the expanded stent as deployed in the artery. More preferably, the total dose or amount of cilostazol available from the drug eluting stent is between 0.56 and 1.53 micrograms per square millimeter of arterial tissue.

As set forth above, the bioresorbable polymer utilized in the composition comprises PLGA. More preferably, the composition comprises a PLGA polymer where the molar ratio of lactide to glycolide residues (L:G) in the polymer chain is from about 90:10 to about 25:75. Even more preferably, the composition comprises a PLGA polymer where the molar ratio of lactide to glycolide residues (L:G) in the polymer chain is from about 80:20 to about 45:55. The PLGA should preferably have an intrinsic viscosity in the range from about 0.1 to about 0.9. Even more preferably, the PLGA should have an intrinsic viscosity in the range from about 0.4 to about 0.7. The weight ratio of cilostazol to PLGA, designated as the D/P ratio, is preferably in the range from about 35/65 to about 95/5, and more preferably from about 47/53 to about 86/14. All ratios are weight percentages. Alternatively, the relative weight proportions of cilostazol and PLGA may be expressed in a normalized form, D:P. Accordingly, the preferred D:P ratio is in the range from about 1:0.05 to about 1:2.0 and more preferably from about 1:0.16 to about 1:1.20.

In order to make the above-described constituents a solution for filling or loading purposes, a suitable solvent is required. Dimethyl sulfoxide, DMSO is the preferred solvent and is preferably utilized in an amount in the range from about 0.01 percent to about 20 percent by weight relative to the weight of cilostazol. Even more preferably DMSO is utilized in an amount in the range from about 1 percent to about 15 percent by weight relative to the weight of cilostazol. Even yet more preferably DMSO is utilized in an amount in the range from about 3 percent to about 12 percent by weight relative to the weight of cilostazol.

As set forth herein, the stents may be fabricated from any suitable biocompatible material. In this exemplary embodiment, the stent is preferably made out of a cobalt-chromium alloy. In addition, the ratio of polymers in the PLGA may be varied. For example, the PLGA may have an L:G ratio from about 100:0 to about 0:100, more preferably from about 50:50 to about 85:15 and more preferably from about 60:40 to about 80:20.

The unique design or construct of the dual drug eluting stent of the present invention provides for completely independent elution rates for the sirolimus and the cilostazol. In addition, this unique construction provides for the sirolimus to be delivered in predominantly a mural or abluminal direction while the cilostazol is delivered in predominantly the luminal direction.

Figure 29:
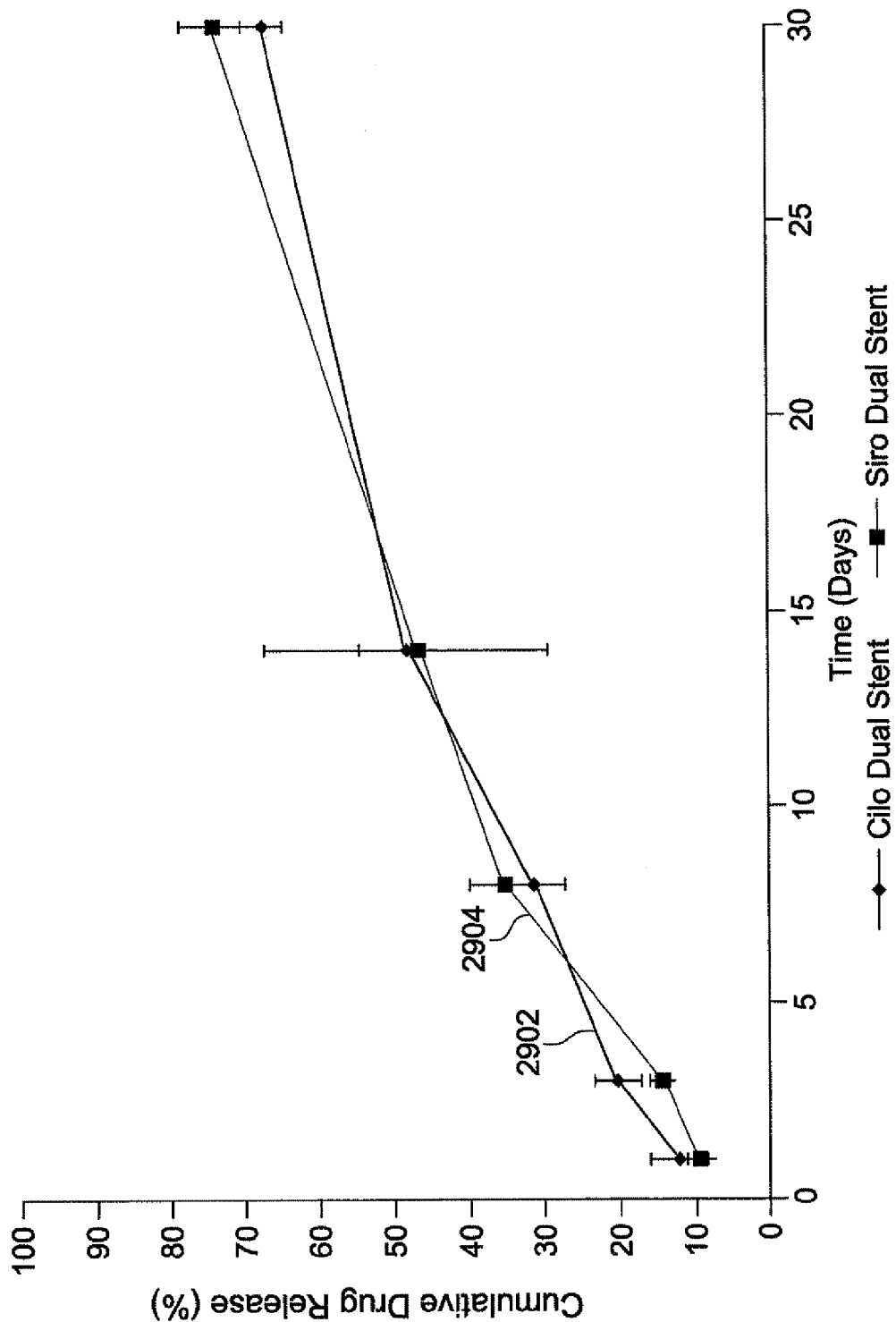
FIG. 29 is a graphical representation of the cumulative in vivo drug release by percent.
Figure 30:
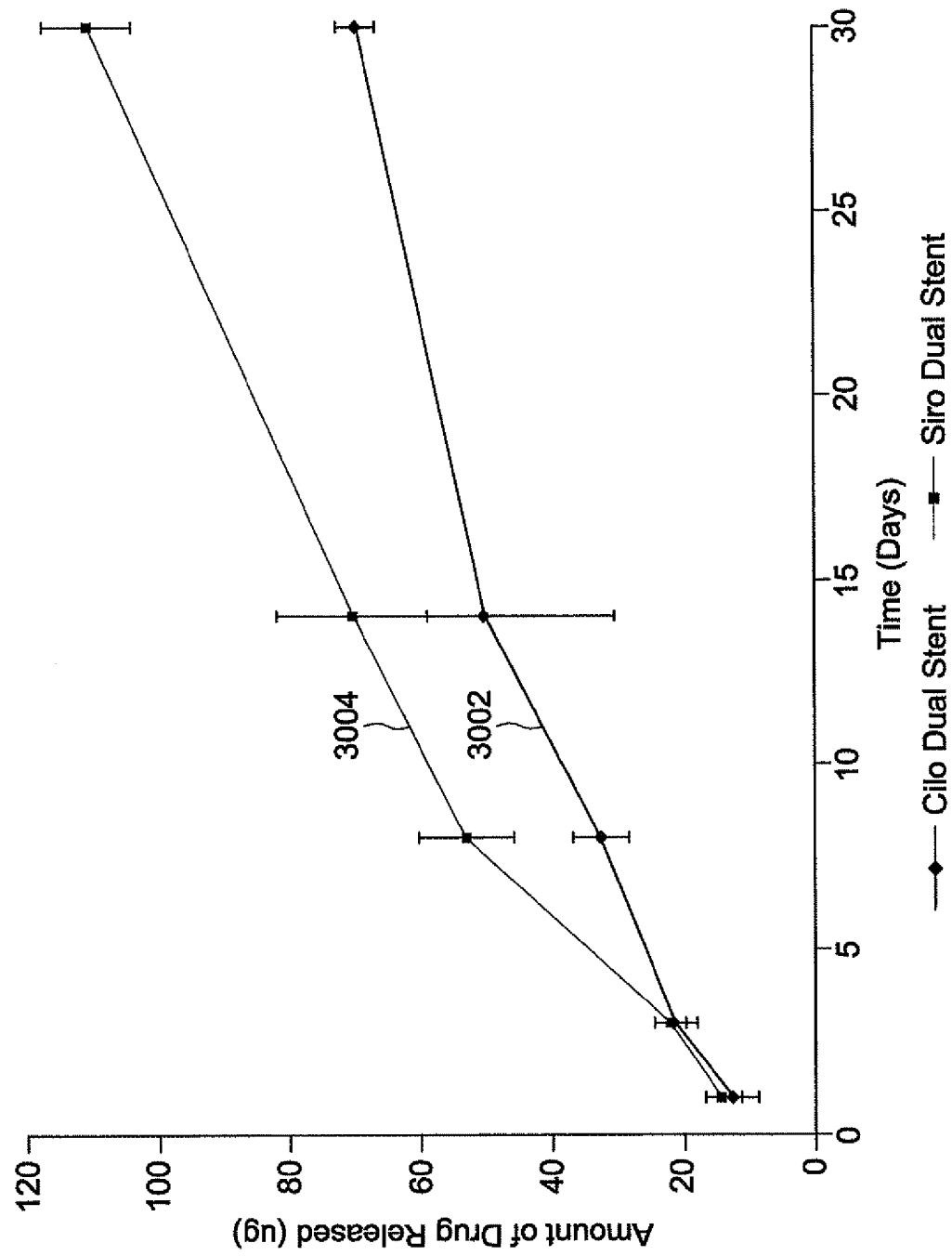
FIG. 30 is a graphical representation of the cumulative in vivo drug release by weight for sirolimus and cilostazol.

Referring to FIG. 29, there is illustrated the cumulative in vivo drug release percentages from a reservoir eluting stent for each drug over a thirty day period. Curve 2902 represents the profile for cilostazol while curve 2904 represents the profile for sirolimus. FIG. 30 is a graphical representation of the amount of each drug, in micrograms, released in vivo. Curve 3002 represents the profile for cilostazol while curve 3004 represents the profile for sirolimus. The curves in the figures illustrate that both the drugs elute independently of each other with minimal or substantially no interaction. About sixty (60) to seventy (70) percent elution was observed at the thirty (30) day time point for both of the drugs. Since the amount of drug (by weight) is different for the drugs in their respective reservoirs, the total amount of drug released at thirty (30) days was higher for sirolimus as compared to cilostazol.

It is important to note that the drug loading or doses for each drug may be expressed in any number of ways, including those set forth above. In a preferred exemplary embodiment, the dose ranges may be expressed as nested absolute ranges of drug weight based on a standard 3.5 mm×17 mm stent size. In this way, the dose ranges would scale with stent size and reservoir count. For example, in a 3.5 mm×17 mm stent size the number of holes or reservoirs is 585. In other exemplary embodiments, the number of reservoirs for a given size stent may include 211 reservoirs for a 2.5 mm×8 mm stent, 238 for a 3.0 mm×8 mm stent, 290 reservoirs for a 3.5 mm×8 mm stent, 311 reservoirs for a 2.5 mm×12 mm stent, 347 for a 3.0 mm×12 mm stent, 417 reservoirs for a 3.5 mm×12 mm stent, 431 reservoirs for a 2.5 mm×17 mm stent, 501 for a 3.0 mm×17 mm stent, 551 reservoirs for a 2.5 mm×22 mm stent, 633 for a 3.0 mm×22 mm stent, 753 reservoirs for a 3.5 mm×22 mm stent, 711 reservoirs for a 2.5 mm×28 mm stent, 809 for a 3.0 mm×28 mm stent, 949 reservoirs for a 3.5 mm×28 mm stent, 831 reservoirs for a 2.5 mm×33 mm stent, 963 for a 3.0 mm×33 mm stent and 1117 reservoirs for a 3.5 mm×33 mm stent. The dose ranges given herein will cover reservoir ratios of sirolimus containing reservoirs to cilostazol containing reservoirs of 20 percent/80 percent to 80 percent/20 percent. The load or dose of sirolimus on a 3.5 mm×17 mm stent may be in the range from about 30 micrograms to about 265 micrograms, more preferably from about 130 micrograms to about 200 micrograms and even more preferably from about 150 micrograms to about 180 micrograms. It is important to note that these are exemplary sizes and reservoir counts. The load or dose of cilostazol on the same 3.5 mm×17 mm stent may be in the range from about 50 micrograms to about 200 micrograms, more preferably from about 90 micrograms to about 200 micrograms and even more preferably from about 100 micrograms to about 150 micrograms. As stated above, the dose ranges would scale with stent size and reservoir count. These doses are for the final sterilized stent product.

The dual drug eluting stent of the invention may be utilized to treat a number of disease states as set forth above, including restenosis, thrombosis, acute myocardial infarction, reprofusion injury, capillary no-reflow conditions, ischemic related conditions and/or to enhance the response of diabetic patients to the antirestenotic effects of sirolimus. In addition to the use of sirolimus and cilostazol, other drugs may be added to the device. For example, as set forth above, anti-thrombotic agents such as heparin may be added. The additional drugs may be included as coatings or in reservoirs. What is important to note is that any number of drugs and reservoir combinations as well as coatings may be utilized to tailor the device to a particular disease state.

Other drugs in the class of cilostazol include milrinone, vesnarionone, enoximone, pimobendan, inamrinone, cilostamide, saterinone, motapizone, lixazinone, imazodan, Pletal, Primacor, Amrinone Lactate and meribendan.

It is also important to note that the duration of release may also be tailored. For example, the in vitro release for sirolimus may be from about 7 to about 120 days and more preferably from about 14 to about 90 days while the in vitro release for cilostazol may be from about 5 to about 61 days. The release states may be tailored for each different drug.

In accordance with another exemplary embodiment, the present invention is directed to a vascular, cobalt-chromium alloy, rapamycin filled reservoir eluting stent, wherein the reservoirs comprise a composition that releases sirolimus (a rapamycin) predominantly in the mural or abluminal direction. Accordingly, the sirolimus will elute locally into the arterial tissue and treat and mitigate restenosis in the artery.

Figure 31:
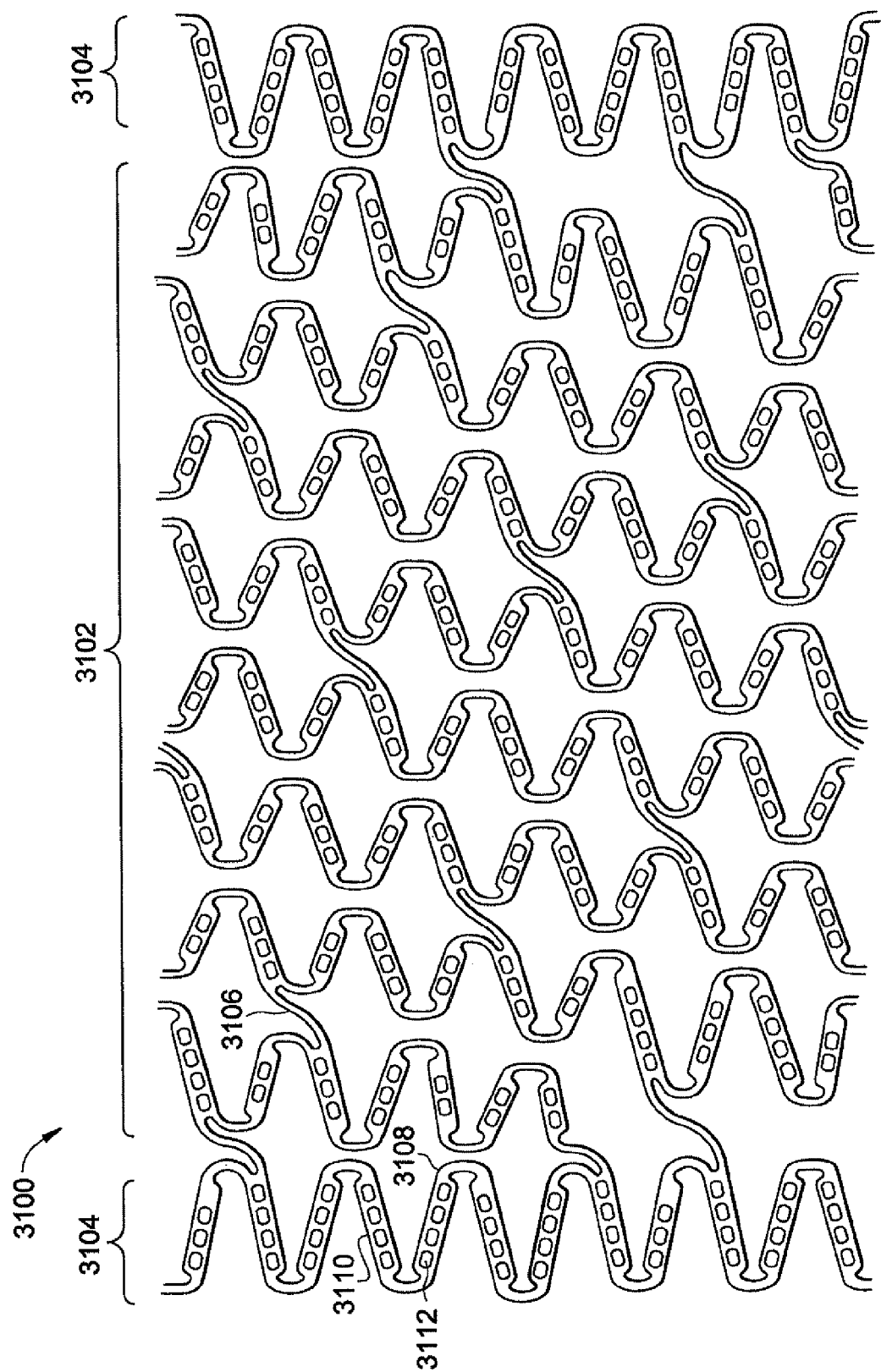
FIG. 31 is a planar view of an alternate embodiment of a stent in accordance with the present invention.

In this exemplary embodiment, a stent comprising a modified geometry is utilized. FIG. 31 is a planar illustration of a stent 3100 having this modified geometry. The basic architecture of the stent 3100 includes a helical interior section 3102, ring-like end sections 3104 and bridges or connectors 3106 distributed throughout the stent 3100 for structural stability under a variety of loading conditions. The stent 3100 also includes ductile hinges 3108 or regions of localized deformation that connect struts 3110 to create the overall structure of the stent 3100. The stent 3100 also includes drug delivery reservoirs 3112 distributed nearly uniformly throughout the stent 3100. As described above, the drug delivery reservoirs 3112 are holes in the struts 3100 that may be filled with a polymer or polymer blend that contains one or more therapeutic agents.

Figure 32:
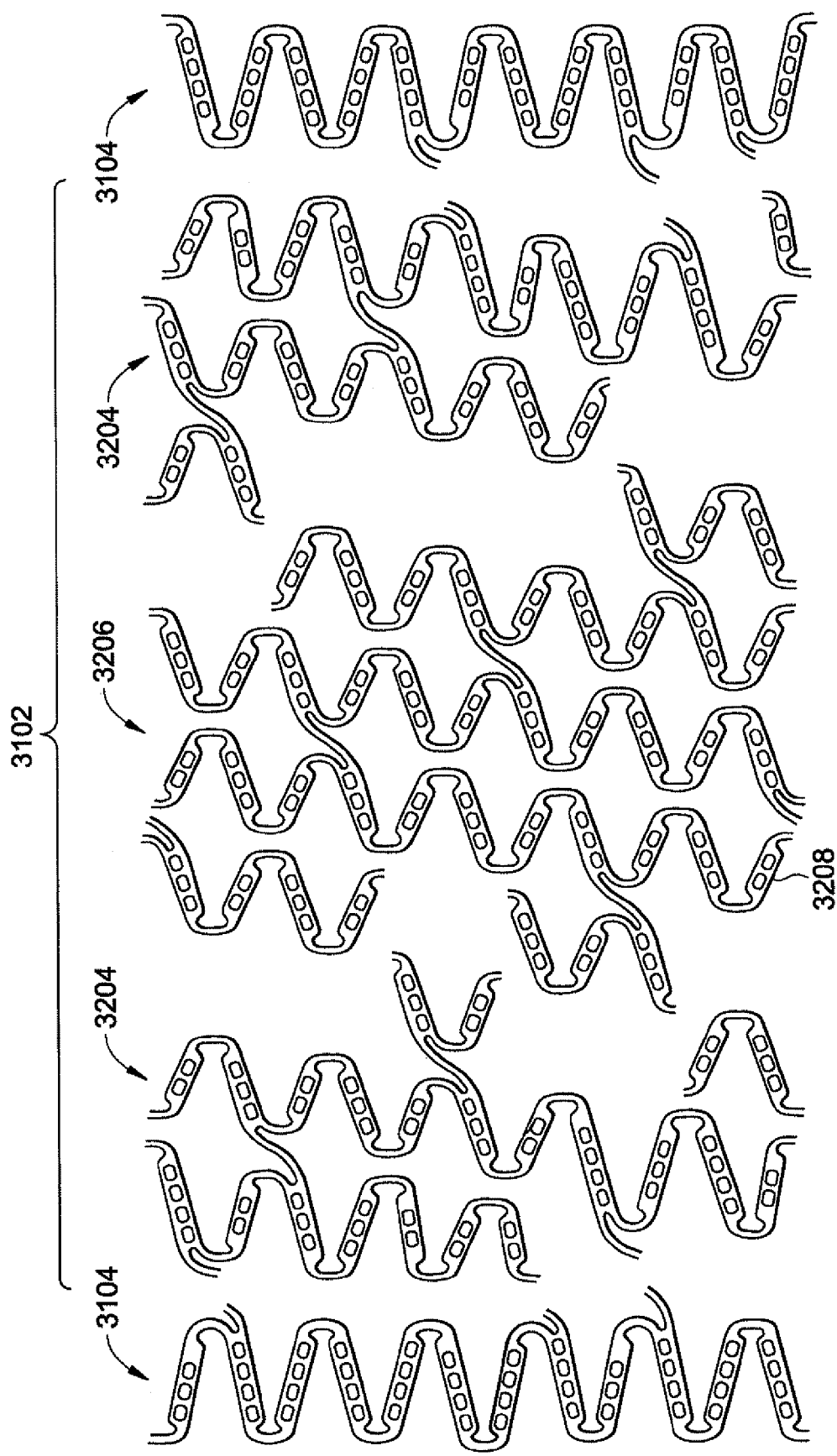
FIG. 32 is a detailed planar view of the stent in FIG. 31.

The ring-like end sections 3104 comprise a sinusoidal arrangement of alternating struts 3110 connected via the ductile hinges 3108. Between the ring-like end sections 3104 is the helical interior section 3102, whereas the name implies, the struts 3110 follow a helical path. The helical path of the interior section 3102 may be achieved by arranging the struts 3110 in a repeating pattern of alternating short and long lengths. The helical interior section 3102 may be further divided into transition zones 3204 and a central zone 3206 as illustrated in FIG. 32 and described herein. The central zone 3206 comprises repeating strut strings 3208 which are geometrically self-symmetric. Accordingly, the central zone 3206 has a constant helical pitch. The transition zones 3204 are sections of variable pitch in which there is no repeatability or geometric self-symmetry. The transition zones 3204 are contrived so as to provide a gradual decrease in pitch between the central zone 3206 and the non-helical ring-like end sections 3104. The transition zones 3204 are connected to the ring-like end sections 3104 by a connecting geometry called an anchor.

As described above, there is a ductile hinge 3108 between every strut pair. The ductile hinge 3108 is a deformable element that is generally substantially thinner than the surrounding struts 3110. The struts 3110 are much stiffer than the ductile hinges 3108 and therefore do not experience any plastic deformation during stent expansion. The struts 3110 essentially rotate as rigid bodies, while the ductile hinges 3108 are designed to bear the plastic strains associated with expansion. As a result, the polymer in the reservoirs 3112 in the struts 3110 are shielded from undue stress during expansion that may cause damage or dislodgment of the polymer. The polymer is ideally in a stress-free state through the stent deployment process.

The design of the ductile hinges 3108 may be optimized through the use of width tapering, such that they offer sufficient radial stiffness to the stent 3100 while simultaneously ensuring that peak plastic strains at full expansion do not exceed the strain carrying capability of the material. This width tapering may be optimized for any ductile hinge to achieve a smooth and uniform distribution of plastic strains along the length of the ductile hinge 3108. By smoothing the strain distribution and thus eliminating strain concentrations in the ductile hinge 3108, its width may be maximized to maximize the stiffness. Maximizing the stiffness of the ductile hinge 3108 is advantageous in that it increases the radial stiffness and fatigue durability of the stent 3100.

In general, the width of the ductile hinge 3108 gradually increases while approaching the root of the hinges 3108 where the hinge 3108 meets an abrupt transition into the wider struts 3110. This prevents plastic strains from connecting at the roots of the hinge 3108. The tapered hinge root is stiffer and therefore distributes plastic strain to the central portion of the hinge 3108. The central portion of the ductile hinge 3108 generally has a uniform width.

It is important to note that the above-described sent 3100 may comprise elements having modified components or elements. For example, variations may occur in the ductile hinge 3108, in the struts 3110, in the connectors 3106 and in the reservoirs 3112.

As set forth above, the exemplary stent described herein comprises a cobalt-chromium alloy. In accordance with the present invention, a cobalt-chromium alloy such as L605 may be utilized to fabricate the stent. A traditional cobalt-based alloy such as L605 (i.e., UNS R30605) which is also broadly utilized as an implantable, biocompatible device material may comprise chromium (Cr) in the range from about 19 to 21 weight percent, tungsten (W) in the range from about 14 to 16 weight percent, nickel (Ni) in the range from about 9 to 11 weight percent, iron (Fe) in the range up to 3 weight percent, manganese (Mn) in the range up to 2 weight percent, silicon (Si) in the range up to 1 weight percent, with cobalt (cobalt) comprising the balance (approximately 49 weight percent) of the composition.

Alternately, another traditional cobalt-based alloy such as Haynes 188 (i.e., UNS R30188) which is also broadly utilized as an implantable, biocompatible device material may comprise nickel (Ni) the range from about 20 to 24 weight percent, chromium (Cr) in the range from about 21 to 23 weight percent, tungsten (W) in the range from about 13 to 15 weight percent, iron (Fe) in the range up to 3 weight percent, manganese (Mn) in the range up to 1.25 weight percent, silicon (Si) in the range from about 0.2 to 0.5 weight percent, lanathanum (La) in the range from about 0.02 to 0.12 weight percent, boron (B) in the range up to 0.015 weight percent with cobalt (Co) comprising the balance (approximately 38 weight percent) of the composition.

In general, elemental additions such as chromium (Cr), nickel (Ni), tungsten (W), manganese (Mn), silicon (Si) and molybdenum (Mo) were added to iron- and/or cobalt-based alloys, where appropriate, to increase or enable desirable performance attributes, including strength, machinability and corrosion resistance within clinically relevant usage conditions.

In this exemplary embodiment of the vascular, cobalt-chromium alloy, rapamycin filled reservoir eluting stent, a composition of a polymer and sirolimus provides for the controlled, sustained local delivery of the sirolimus from the reservoirs of the sent abluminally to the arterial tissue of the patient.

The composition in accordance with the present invention is loaded into the reservoirs 3112 in a sequential series of steps, including depositing a fluid filling solution composition into the reservoirs 3112 and evaporating a majority, if not substantially all, of the filling solution solvent. Having no solvent in the final composition is the ideal situation. It should be appreciated that any suitable deposit process may be utilized as described herein. The composition in accordance with the present invention as described above is the solid materials that remain in the reservoir 3112 after removal of substantially all or preferably all of the solvent from the filling solution composition.

The fluid compositions used to form the solid composition comprising sirolimus include a bioresorbable or bioabsorbable polymer, preferably a poly(lactide-co-glycolide), PLGA, polymer, a suitable solvent such as dimethyl sulfoxide, DMSO, or N-methyl pyrrolidinone, NMP, sirolimus and optionally a stabilizer or anti-oxidant such as butylated hydroxy toluene or BHT. An alternate spelling for BHT is butylated hydroxtoluene. Preferably, at least one of the fluid filling solution compositions utilized in a deposition step to create the final sirolimus compositions in the stent reservoir 3112 comprises BHT.

Alternatives for BHT include butylated hydroxyl anisole, BHA, gallate esters such as propyl gallate or ascorbate esters such as palmitoyl ascorbate. BHT is preferred based upon its high level of effectiveness in stabilizing sirolimus, its low level toxicity and its hydrophobicity. BHT elutes from the reservoirs 3112 at approximately the same rate as sirolimus and as such there is preferably BHT present with the sirolimus. Alternatives for DMSO and NMP include dimethyl acetomide (DMAc) or dimethyl formamide (DMF). DMSO is preferred because sirolimus is more stable in the presence of DMSO.

Each sequential fluid composition that is deposited may comprise the same ingredients or constituents, or sequential filling solutions may be prepared from filling solutions comprising different ingredients or constituents. Preferably, the first series of filling solution deposits comprise only polymer and solvent, which, as described above, are dried after each filling step. This part of the process results in the formation of a base structure. Once the base structure is formed, subsequent solutions comprising polymer, solvent, sirolimus and BHT are added and are also dried after each filling step. This manufacturing sequence will create a reservoir composition in which there is a lower concentration of sirolimus in the area of the luminal surface of the stent 3100 and a relatively higher concentration of sirolimus in the area of the mural or abluminal face of the stent 3100. This configuration creates a longer path or higher resistance to elution of the drug to the luminal face areas compared to the mural or abluminal face and as such should result in substantially all of the sirolimus being delivered to the mural or abluminal side of the stent 3100 and into the arterial tissues.

The sirolimus composition within a reservoir 3112 will preferably comprise sirolimus, a bioresorbable polymer, a stabilizing agent and a solvent, wherein each of the components will be in the certain proportion relative to one another. Preferably, the total dose or amount of sirolimus available from the stent 3100 is between 0.15 and 2.7 micrograms per square millimeter of arterial tissue area, where the area of arterial tissue is defined as the area of the surface of a theoretical cylinder whose diameter and length are the diameter and length of the expanded stent 3100 as deployed in the artery. More preferably, the total dose or amount of sirolimus available from the stent 3100 is between 0.7 and 1.2 micrograms per square millimeter of arterial tissue.

As set forth above, the bioresorbable polymer utilized in the composition comprises PLGA. More preferably, the composition comprise a PLGA polymer where the molar ratio of lactide to glycolide residues (L:G) in the polymer chain is from about 100:0 to about 50:50. Even more preferably, the composition comprises a PLGA polymer where the molar ratio of lactide to glycolide residues (L:G) in the polymer chain is from about 80:20 to about 70:30. The weight ratio of sirolimus to PLGA, designated as the D:P ratio is preferably in the range from about 30/70 to about 60/40, and more preferably from about 42/58 to about 50/50. All ratios are weight percentages. Alternatively, the relative weight proportion of sirolimus and PLGA may be expressed in a normalized form, D:P. Accordingly, the preferred D:P ratio is in the range from about 1:0.66 to about 1:2.3 and more preferably from about 1:1.00 to about 1:1.38.

Also as described above, the sirolimus composition preferably comprises BHT, butylated hydroxy toluene or butylated hydroxytoluene. The amount of BHT added is preferably less than about 3 percent by weight of the amount of sirolimus. Even more preferably, the amount of BHT added is in the range from about 1.2 percent by weight to about 2.6 percent by weight of the amount of sirolimus.

In order to make the above-described constituents a solution for deposition purposes, a suitable solvent is required. Dimethyl sulfoxide, DMSO, is the preferred solvent and is preferably utilized in the present invention. The amount present is in the range from about 0.01 percent to about 20 percent by weight relative to the weight of sirolimus. Even more preferably, DMSO is utilized in an amount in the range from about 1 percent to about 15 percent by weight relative to the weight of sirolimus. Even yet more preferably, DMSO is utilized in an amount in the range from about 4 percent to about 12 percent by weight relative to the weight of sirolimus.

It is important to note that the drug loading or doses for each drug may be expressed in any number of ways, including those set forth above. In a preferred exemplary embodiment, the dose ranges may be expressed as nested absolute ranges of drug weight based on a standard 3.5 mm×17 mm stent size. In this way, the dose ranges would scale with stent size and reservoir count. For example, in a 3.5 mm×17 mm stent size the number of holes or reservoirs is 585. In other exemplary embodiments, the number of reservoirs for a given size stent may include 211 reservoirs for a 2.5 mm×8 mm stent, 238 for a 3.0 mm×8 mm stent, 290 reservoirs for a 3.5 mm×8 mm stent, 311 reservoirs for a 2.5 mm×12 mm stent, 347 for a 3.0 mm×12 mm stent, 417 reservoirs for a 3.5 mm×12 mm stent, 431 reservoirs for a 2.5 mm×17 mm stent, 501 for a 3.0 mm×17 mm stent, 551 reservoirs for a 2.5 mm×22 mm stent, 633 for a 3.0 mm×22 mm stent, 753 reservoirs for a 3.5 mm×22 mm stent, 711 reservoirs for a 2.5 mm×28 mm stent, 809 for a 3.0 mm×28 mm stent, 949 reservoirs for a 3.5 mm×28 mm stent, 831 reservoirs for a 2.5 mm×33 mm stent, 963 for a 3.0 mm×33 mm stent and 1117 reservoirs for a 3.5 mm×33 mm stent. The load or dose of sirolimus on a 3.5 mm×17 mm stent may be in the range from about 30 micrograms to about 500 micrograms, more preferably from about 130 micrograms to about 200 micrograms and even more preferably from about 140 micrograms to about 185 micrograms. It is important to note that these are exemplary sizes and reservoir counts. As stated above, the dose ranges would scale with stent size and reservoir count. These doses are for the final sterilized stent product.

It is also important to note that the duration of release may also be tailored. For example, the in vivo release for sirolimus may be from about 7 to about 120 days and more preferably from about 14 to about 90 days.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A drug filled reservoir eluting implantable medical device comprising:
a stent comprising a helical mid section formed from a substantially sinusoidal arrangement of struts with alternating orientation configured to have a constant helical pitch connected via ductile hinges, the helical mid section comprising repeating strut strings that are geometrically self-symmetric, first and second ring end sections having a substantially sinusoidal arrangement of struts with alternating orientation connected via ductile hinges, and first and second transition zones in which there is no repeatability or geometric self-symmetry of the struts, the first and second transition zones having a variable pitch and formed from a substantially sinusoidal arrangement of struts with alternating orientation connected via ductile hinges, such that the first and second transition zones provide a gradual decrease in pitch between the helical mid section and the first and second ring end sections, the first and second ring end sections being connected to the helical mid section via the first and second helical transition sections respectively, wherein at least one of the struts comprise at least one reservoir; and a composition comprising an mTOR inhibitor and a biodegradable polymer, the composition being deposited in the at least one reservoir and configured to elute the mTOR inhibitor in the abluminal direction.

2. The drug filled reservoir eluting implantable medical device according to claim 1, wherein the stent comprises a cobalt-chromium alloy.

3. The drug filled reservoir eluting Implantable medical device according to claim 2, wherein the composition comprises rapamycin and poly(lactide-co-glycolide).

4. The drug filled reservoir eluting implantable medical device according to claim 3, wherein the rapamycin comprises sirolimus.

5. The drug filled reservoir eluting implantable medical device according to claim 4, further comprising a stabilizing agent.

6. The drug filled reservoir eluting implantable medical device according to claim 5, wherein the stabilizing agent comprises butylated hydroxyl toluene.

* * * * *